US008673606B2

(12) United States Patent
Menashe

(10) Patent No.: US 8,673,606 B2
(45) Date of Patent: Mar. 18, 2014

(54) MICROORGANISM COMPRISING PARTICLES AND USES OF SAME

(76) Inventor: Ofir Menashe, Shimshit (IL)

( * ) Notice: Subject to any disclaimer, the term of this patent is extended or adjusted under 35 U.S.C. 154(b) by 105 days.

(21) Appl. No.: 13/130,584

(22) PCT Filed: Mar. 25, 2010

(86) PCT No.: PCT/IL2010/000256
§ 371 (c)(1),
(2), (4) Date: May 23, 2011

(87) PCT Pub. No.: WO2010/122545
PCT Pub. Date: Oct. 28, 2010

(65) Prior Publication Data
US 2011/0229930 A1    Sep. 22, 2011

Related U.S. Application Data

(60) Provisional application No. 61/171,478, filed on Apr. 22, 2009.

(51) Int. Cl.
| C12N 11/08 | (2006.01) |
| C12N 1/20 | (2006.01) |
| C02F 3/34 | (2006.01) |
| C12P 1/00 | (2006.01) |

(52) U.S. Cl.
USPC ............. 435/180; 435/174; 435/183; 435/41; 435/262; 435/243; 435/252.1; 210/601

(58) Field of Classification Search
USPC ........ 435/174, 180, 183, 41, 262, 243, 252.1; 210/601
See application file for complete search history.

(56) References Cited

U.S. PATENT DOCUMENTS

| 3,883,397 | A | 5/1975 | Townsley |
| 4,530,763 | A | 7/1985 | Clyde et al. |
| 5,275,943 | A | 1/1994 | DiTuro |
| 5,348,803 | A | 9/1994 | Schlaemus et al. |
| 5,543,309 | A | 8/1996 | Pischel |
| 5,877,113 | A | 3/1999 | Mehta |
| 6,110,372 | A | 8/2000 | Perriello |
| 6,303,144 | B1 | 10/2001 | Omura |
| 6,451,585 | B1 | 9/2002 | Kirschner |
| 6,705,391 | B1 * | 3/2004 | Lewin ........................... 165/133 |
| 6,863,816 | B2 * | 3/2005 | Austin et al. ................... 210/602 |
| 2002/0098982 | A1 * | 7/2002 | Burnham ....................... 504/359 |
| 2003/0113903 | A1 | 6/2003 | Miyazaki |
| 2003/0219888 | A1 | 11/2003 | Segall et al. |
| 2004/0175412 | A1 | 9/2004 | Asada et al. |
| 2009/0258051 | A1 * | 10/2009 | Chidambaram et al. ...... 424/423 |
| 2009/0274766 | A1 * | 11/2009 | Marash et al. ................ 424/497 |
| 2010/0303962 | A1 * | 12/2010 | Penhasi et al. .................. 426/61 |
| 2011/0008493 | A1 * | 1/2011 | Zorea .............................. 426/61 |
| 2011/0236538 | A1 * | 9/2011 | Ochoa Mendoza et al. .. 426/103 |

FOREIGN PATENT DOCUMENTS

| EP | 1053752 | 11/2000 |
| EP | 1407678 | 4/2004 |
| WO | WO 97/37008 | 10/1997 |
| WO | WO 2008/035332 | 3/2008 |
| WO | WO 2010/122545 | 10/2010 |

OTHER PUBLICATIONS

International Search Report and the Written Opinion Dated Jul. 13, 2010 From the International Searching Authority Re. Application No. PCT/IL10/00256.
Dvorak et al. "The Use of Nitrous Oxide for Producing Eupolyploids and Aneuploids in Wheat and Barley", Canadian Journal of Genetics and Cytology, 15(1): 205-214, 1973.
Office Action Dated Feb. 14, 2013 From the Israel Patent Office Re. Application No. 213072 and Its Translation Into English.
Communication Relating to the Results of the Partial International Search Dated Sep. 14, 2012 From the European Patent Office Re. Application No. PCT/IB2012/052589.
International Preliminary Report on Patentability Dated Nov. 3, 2011 From the International Bureau of WIPO Re. Application No. PCT/IL2010/000256.
Fragata "A Hypothesis Concerning the Use of Colchicine as a Polyploidy Inducer", Experientia, 26(1): 104-106, Jan. 15, 1970.
International Search Report and the Written Opinion Dated Jan. 18, 2013 From the International Searching Authority Re. Application No. PCT/IB2012/052589.
Menashe "Microencapsulation of Microbial Cells", BioCastle Water Technologies Ltd., p. 1-6, Feb. 2013.
Rathore et al. "Microencapsulation of Microbial Cells", Journal of Food Engineering, 116: 369-381, 2013.
Supplementary European Search Report and the European Search Opinion Dated Sep. 24, 2013 From the European Patent Office Re. Application No. 10766735.4.

* cited by examiner

Primary Examiner — Susan Hanley

(57) ABSTRACT

A particle is disclosed. The particle comprising: (i) at least one inner core which comprises a solid matrix of nutrients for microorganism growth; (ii) an inner membrane being fabricated from a water-soluble polymer, the inner membrane surrounding the inner core and a population of dried microorganisms; and (iii) an outer porous membrane surrounding the inner membrane, the outer porous membrane being insoluble in water. Methods of generating same, propagating microorganisms within and uses of same are also disclosed.

24 Claims, 19 Drawing Sheets
(9 of 19 Drawing Sheet(s) Filed in Color)

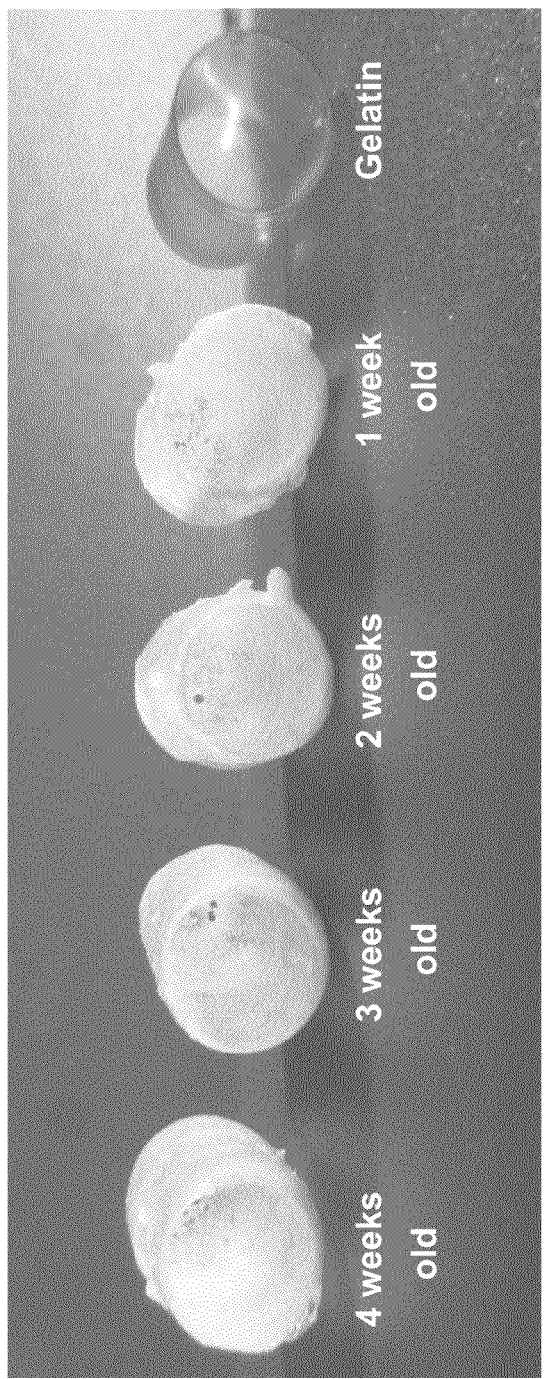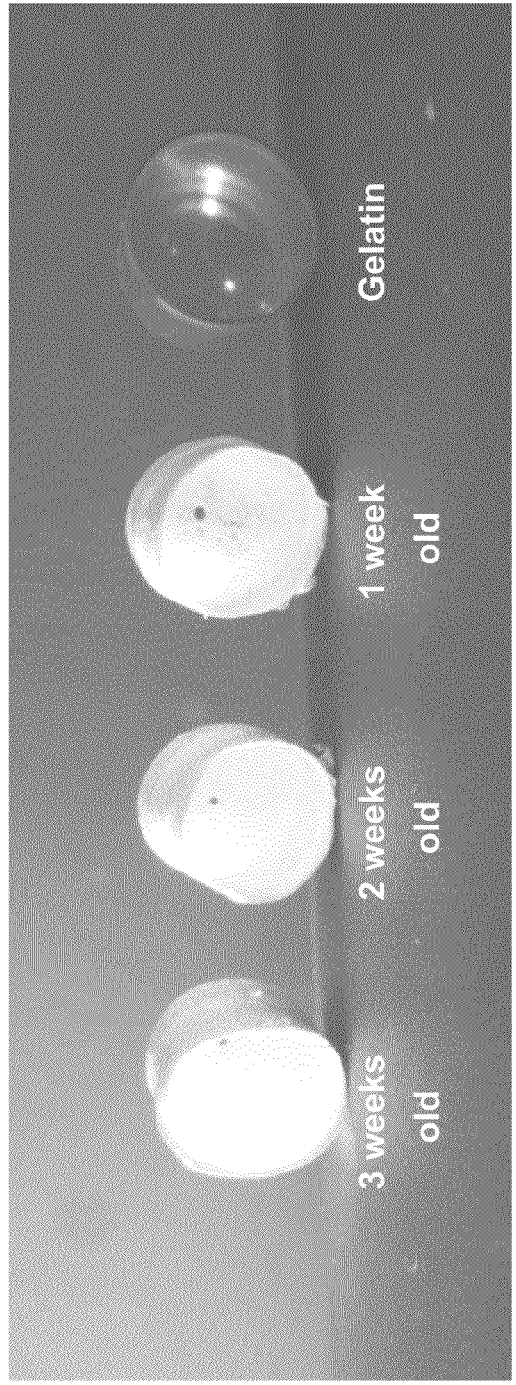
FIG. 7A
FIG. 7B

MICROORGANISM COMPRISING PARTICLES AND USES OF SAME

RELATED APPLICATIONS

This application is a National Phase of PCT Patent Application No. PCT/IL2010/000256 having International filing date of Mar. 25, 2010, which claims the benefit of priority of U.S. Provisional Patent Application No. 61/171,478 filed on Apr. 22, 2009. The contents of the above applications are all incorporated herein by reference.

FIELD AND BACKGROUND OF THE INVENTION

The present invention, in some embodiments thereof, relates to microorganism-comprising particles and, more particularly, but not exclusively, to the use of same for the removal of contaminants from water or soil, for treatment of diseases and for the production of pharmaceutical and cosmetic compositions.

Water quality management is one of the world's most significant concerns. As industry becomes more complex and advanced, problems associated with water pollution become more significant. Consequently, advanced wastewater treatment technology is required. Concentration of industrial waste nutrients such as heavy metals, phosphorous, phenols and oils are difficult to reduce to safe environmental levels. Increasing environmental awareness and the toughening governmental policies, demand new environmentally friendly ways to clean up contaminants using low cost methods and materials. These new technologies for removing nutrients from large volume of wastewater must be economically feasible. For example, physicochemical procedures, such as chemical precipitation, utilizing flocculation-coagulation-sedimentation processes and ion exchange adsorption to exclude heavy metals from wastewater are currently used.

Biological materials and methods, have been extensively studied, and answer some of the above demands, being both economically feasible and capable of coping with large volumes of wastewater.

Biosorption (the ability of certain types of inactive, dead, microbial biomass to bind and concentrate heavy metals from even very diluted aqueous solutions) has proven to be an excellent way to treat industrial waste effluents, offering significant advantages such as low cost, availability, efficiency and ease of operation. Biosorption from aqueous effluents has become a potential alternative to the existing technologies of removal hazard nutrients from industrial wastewater [Shuttleworth, K. L. and R. F. Appl Environ Microbiol (1993). 59(5): 1274-1282].

Bioaccumulation, the gradual accumulation of a certain chemical into living organisms, has been used to clean up contaminated environments such as copper-, zinc- and nickel-contaminated wastewater [Kara Y., Int. J. Environ. Sci. Tech. (2005) 2(1): 63-67].

Biodegradation, the process by which live microorganisms are capable of removing contaminants (e.g. nitrates) from organic material has also been extensively used to clean up contaminated environments (e.g. wastewater). Live microorganisms have the naturally occurring, microbial catabolic diversity to degrade, transform or accumulate a huge range of compounds including hydrocarbons (e.g. oil), polychlorinated biphenyls (PCBs), polyaromatic hydrocarbons (PAHs), pharmaceutical substances, radionuclides and metals.

Microorganisms have the ability to remove contaminants (e.g. heavy metals, phosphates and oils) from wastewater by degradation or absorption and the efficiency of such biological processes is high, estimated to give a yield of exclusion of over 99%. As such, a high percentage of ongoing academic research is focused on identifying specialized microorganisms (e.g. bacteria, yeast, fungi and algae) and adapting them to hostile conditions such as wastewater environment. The main challenge is to use living microorganisms in unstable conditions (e.g. pH variations, nutrients inhibition, nutrient enhancement, etc.).

Furthermore, wastewater flora consists of various microorganisms populations co-exiting in a steady state. The efficient use of microorganisms in wastewater treatment requires that the introduced culture be genetically stable and would integrate along with the wastewater natural flora. Introduction of the new culture may be problematic as it may interrupt the flora stability and may lead to undesired effects such as an undesired withdrawal to the former steady state or to elimination of the new microorganisms. Thus, efficiency of the biological process or treatment depends on the threshold concentration (biomass) of the introduced culture. Since the introduced microorganism culture is challenged by natural selection forces (due to environmental adaption), reaching the necessary biomass may be impossible and survival of the introduced culture is extremely difficult.

Biosorption and biodegradation processes using selected bacteria to exclude contaminant nutrients have been commercially previously described. For example, BioPetroClean (BPC) utilizes a bacterial cocktail to remove both dissolved and emulsified hydrocarbons from water, soil, oil storage and transportation tanks. Their technology combines a unique mixture of naturally-occurring bacteria that feed on petroleum hydrocarbons combined with a supplemental nutrient-mix and a controlled oxygen tension and pH which ensures optimal bio-degradation. The BPC technology is based on adaptation of planktonic bacteria blends with the ability to degrade petroleum hydrocarbons.

Furthermore, bioprocessors have frequently been used to grow useful cells or to clean contaminated effluent, such as water. More specifically, biofilms have been widely used because an active biomass produced in the reactor allows large volumetric loadings and good effluent quality without the need for separation of solids. The biofilm bioreactors have been generally categorized as continuously stirred tank reactors (CSTRs), fixed-bed and fluidized bed (described in detail in U.S. Pat. No. 6,235,196).

Numerous publications have described the use of microorganisms to exclude contaminant nutrients such as heavy metals, phosphates and oils from wastewater. Following are some of the cited art.

U.S. Pat. No. 4,530,763 describes methods for treating waste fluids to remove selected chemicals (e.g. minerals and metals) using bacterial cultures. According to their teachings, the bacterial culture is first transferred to a nutrient medium to enable satisfactory bacterial cell growth. The bacterial cells are then attached to a porous fiber webbing supported in a suitable container, the nutrient medium is then replaced with waste fluid for a period of time sufficient to attach the chemical to the bacterial cells. The waste fluid is then removed from the container and the chemical separated from the fiber webbing.

U.S. Pat. No. 6,423,229 describes bioreactor systems for biological nutrient removal. Specifically, U.S. Pat. No. 6,423,229 teaches an integrated biological treatment process and bioreactor system which provides means for simultaneous removal of biodegradable solids, nitrogen and phosphate from water and wastewater. The system comprises microbial consortia immobilized in separate bioreactors for anaerobic processes, phosphate removal and denitrification.

SUMMARY OF THE INVENTION

According to an aspect of some embodiments of the present invention there is provided a particle comprising: (i) at least one inner core which comprises a solid matrix of nutrients for microorganism growth; (ii) an inner membrane being fabricated from a water-soluble polymer, the inner membrane surrounding the inner core and a population of dried microorganisms; and (iii) an outer porous membrane surrounding the inner membrane, the outer porous membrane being insoluble in water.

According to an aspect of some embodiments of the present invention there is provided a method of generating the particle, the method comprising: (a) inserting a solid matrix of nutrients for microorganism growth inside a membrane fabricated from a water-soluble polymer; (b) inserting a population of dried microorganisms into the membrane; and (c) covering the membrane with a water-insoluble porous membrane, thereby producing the particle.

According to an aspect of some embodiments of the present invention there is provided a method of propagating a population of microorganisms, the method comprising: (a) contacting the particle of claim 1 with a liquid under conditions that allow the liquid to penetrate the outer porous membrane and wet the dried microorganisms so as to generate an activated particle; and (b) culturing the activated particle, thereby propagating the population of microorganisms.

According to an aspect of some embodiments of the present invention there is provided a method of purifying water, the method comprising contacting the water with at least one particle under conditions that allow the microorganisms to decontaminate the water, thereby purifying the water.

According to an aspect of some embodiments of the present invention there is provided a method of treating soil contamination, the method comprising: (a) contacting at least one particle with a liquid under conditions that allow the liquid to penetrate the outer porous membrane and wet the dried microorganisms to generate an activated particle; and (b) contacting the soil with the activated particle, thereby treating the soil contamination.

According to an aspect of some embodiments of the present invention there is provided a method of synthesizing a molecule of interest, the method comprising: contacting a plurality of particles with a liquid medium under conditions which allow synthesis of the molecule of interest, wherein each of the plurality of particles comprise: (i) a population of dried microorganisms; (ii) an inner membrane being fabricated from a water-soluble polymer, the inner membrane comprising the population of dried microorganisms, wherein the population of dried microorganisms are capable of synthesizing the molecule of interest on contact with the liquid medium; and (iii) an outer porous membrane surrounding the inner membrane, the outer porous membrane being insoluble in water thereby synthesizing the molecule of interest.

According to an aspect of some embodiments of the present invention there is provided a method of treating a gastrointestinal disorder in a subject in need thereof, the method comprising administering to the subject a therapeutically effective amount of particles, wherein the particles comprise: (i) at least one inner core which comprises a solid matrix of nutrients for microorganism growth; (ii) an inner membrane being fabricated from a water-soluble polymer, the inner membrane comprising the inner core and a population of dried microorganisms, wherein the population of dried microorganism secrete an agent useful for the treatment of the gastrointestinal disorder in the subject; and (iii) an outer porous membrane surrounding the inner membrane, the outer porous membrane being insoluble in water, thereby treating the gastrointestinal disorder in the subject.

According to an aspect of some embodiments of the present invention there is provided a pharmaceutical composition comprising as an active ingredient a plurality of particles and a pharmaceutically acceptable carrier, wherein the plurality of particles comprise: (i) at least one inner core which comprises a solid matrix of nutrients for microorganism growth; (ii) an inner membrane being fabricated from a water-soluble polymer, the inner membrane comprising the inner core and a population of dried microorganisms, wherein the population of dried microorganisms are capable of secreting an agent useful for the treatment of a medical disorder, on contact with a liquid medium; and (iii) an outer porous membrane surrounding the inner membrane, the outer porous membrane being insoluble in water.

According to some embodiments of the invention, the microorganisms are selected for water decontamination.

According to some embodiments of the invention, the microorganisms are selected for soil decontamination.

According to some embodiments of the invention, the microorganisms are selected from the group consisting of bacteria, algae, yeast and fungi.

According to some embodiments of the invention, the microorganisms comprise bacteria.

According to some embodiments of the invention, the bacteria comprise freeze-dried bacteria.

According to some embodiments of the invention, the microorganisms comprise a homogenous population of microorganisms.

According to some embodiments of the invention, the microorganisms comprise a heterogeneous population of microorganisms.

According to some embodiments of the invention, contacting is effected for about 24 to 96 hours.

According to some embodiments of the invention, the solid matrix of nutrients comprises an agar.

According to some embodiments of the invention, the inner core is coated with a control release polymer.

According to some embodiments of the invention, the inner membrane or the inner core further comprise an enzyme.

According to some embodiments of the invention, the inner core further comprises an agent selected from the group consisting of an amino acid, an enzyme, a sugar, an iron, a salt and an essential element.

According to some embodiments of the invention, the inner core is devoid of at least one agent selected from the group consisting of an amino acid, a sugar, an iron, a salt and an essential element.

According to some embodiments of the invention, the particle is capable of supporting biofilm formation within.

According to some embodiments of the invention, the inner membrane further comprises additional elements which support biofilm formation thereon.

According to some embodiments of the invention, the additional elements comprise glass beads.

According to some embodiments of the invention, the inner membrane further comprises activated carbon granules or activated carbon chips within.

According to some embodiments of the invention, the water-soluble polymer comprises gelatin.

According to some embodiments of the invention, the outer porous membrane is fabricated from a polymer selected from the group consisting of PVAL (polyvinyl-alcohol), Polyethersulfone (PES), Cellulose Acetate, Cellulose Nitrate, Ethyl Cellulose, Nitrocellulose Mixed Esters, Polycarbonate film, Nylon, PVDF (poly(vinylidene fluoride)) and Polysulfone.

According to some embodiments of the invention, the outer porous membrane is fabricated from a polymer comprising Cellulose Acetate.

According to some embodiments of the invention, the outer porous membrane is fabricated from a polymer comprising Ethyl Cellulose.

According to some embodiments of the invention, the porous membrane is resistant to biofilm formation.

According to some embodiments of the invention, the pore of the porous membrane is less than 0.85 μM.

According to some embodiments of the invention, the particle is between 0.5-30 cm in length.

According to some embodiments of the invention, the water is wastewater.

According to some embodiments of the invention, the wastewater is selected from the group consisting of Petroleum wastewater, heavy metal wastewater and municipal wastewater.

According to some embodiments of the invention, the water is drinking water.

According to some embodiments of the invention, the at least one particle comprises at least two non-identical particles.

According to some embodiments of the invention, the non-identical particles comprise different populations of microorganisms.

According to some embodiments of the invention, the plurality of particles further comprises at least one inner core.

According to some embodiments of the invention, the particles are pre-activated in a liquid prior to the contacting.

According to some embodiments of the invention, the microorganism is genetically modified so as to synthesize the molecule of interest.

According to some embodiments of the invention, the molecule of interest comprises a polypeptide.

According to some embodiments of the invention, the polypeptide is a secreted polypeptide.

According to some embodiments of the invention, the method further comprises purifying the polypeptide.

According to some embodiments of the invention, the molecule of interest is an antibiotic.

According to some embodiments of the invention, the molecule of interest is selected from the group consisting of an antibiotic, an antibody, an insulin, an interferon, a growth factor, a clotting factor, an enzyme, a diamine, a polyamine, a glycolpeptide, a lipopeptide, a hormone and a steroid.

According to some embodiments of the invention, the administering is orally administering.

According to some embodiments of the invention, the agent comprises a polypeptide.

According to some embodiments of the invention, the agent is selected from the group consisting of an antibiotic, an antibody, an insulin, an interferon, a growth factor, a clotting factor, an enzyme, a diamine, a polyamine, a glycolpeptide, a lipopeptide, a hormone and a steroid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is an illustration of the components of the particle. The particle components comprise (1) an outer semi-permeable membrane (for nanofiltration/microfiltration), (2) a nutrient-comprising inner core, (3) dried microorganisms, (4) optionally, glass/polymer beads and other components such as active carbon (not shown herein) may be added therein.

FIG. 1B is a photograph depicting a particle prototype with a cellulose acetate membrane.

Figure 2:
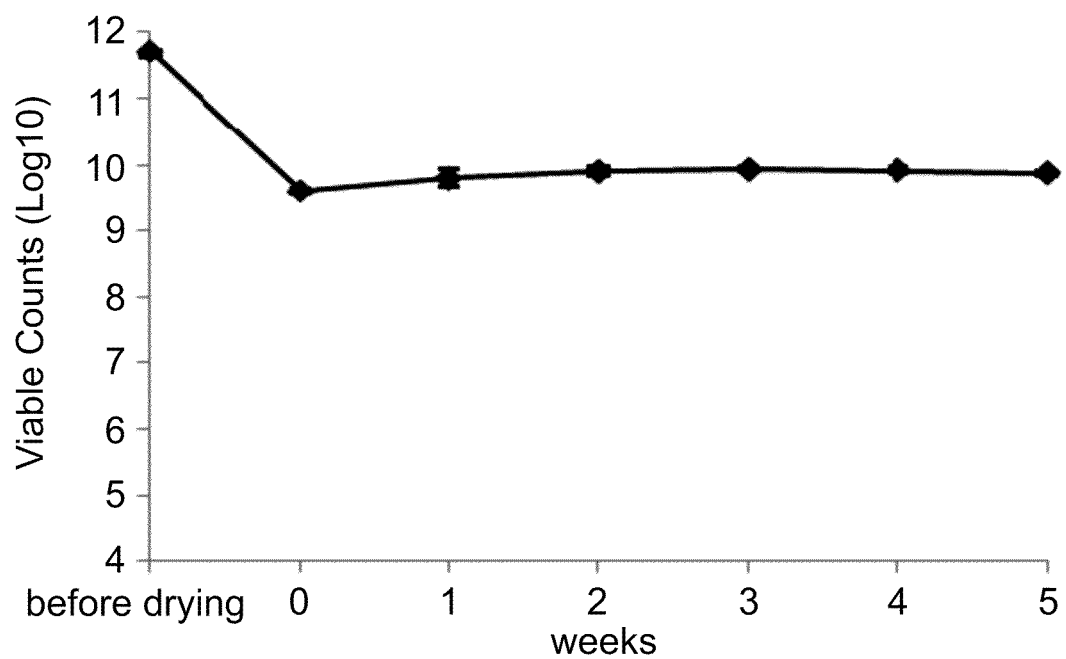

FIG. 2 is a graph depicting viability (log 10) of freeze-dried *E. coli.* bacteria. Of note, the bacteria viability levels were kept stable for at least 5 weeks after rehydration at an average of 9.5 CFU/ml. The recovery rate of the culture was 1.6%-1.8%.

Figure 3:

FIG. 3 is a photograph depicting a freeze-dried *E. coli* TG1 culture.

Figure 4B:
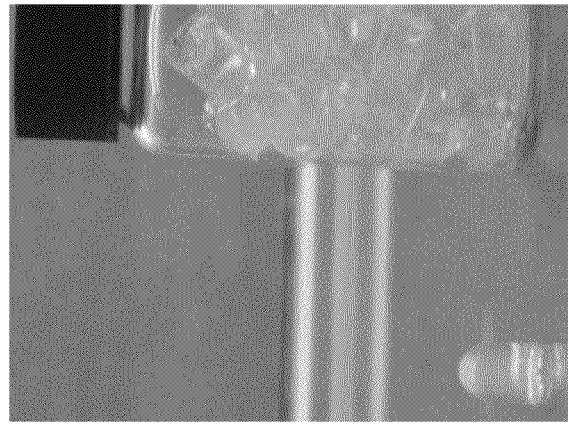
Figure 4A:
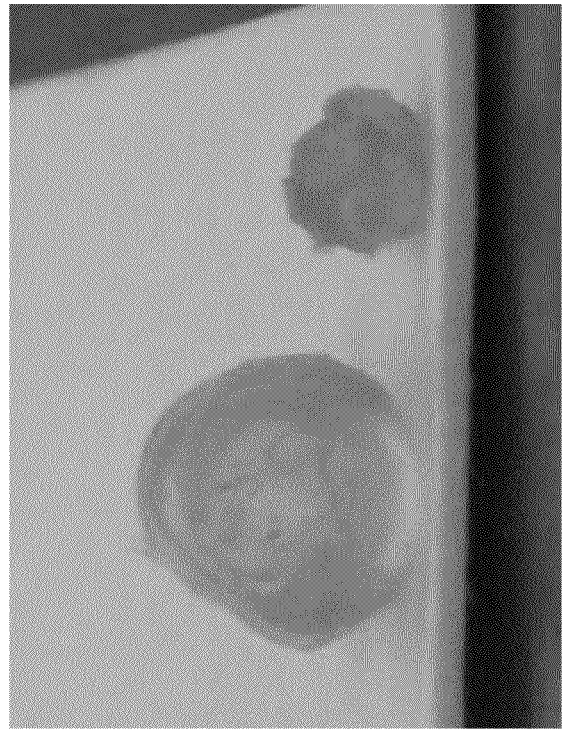

FIGS. 4A-B are photographs depicting the inner core of the particle. FIG. 4A depicts the inner core after polymerization (left) and in comparison to a dried core (right). FIG. 4B depicts a lateral view of an inner core after polymerization and storage of inner cores in a vial (sterilized by U.V radiation).

Figure 5:

FIG. 5 is photograph depicting water soluble gelatin capsules which contain all of the inner components.

Figure 6:
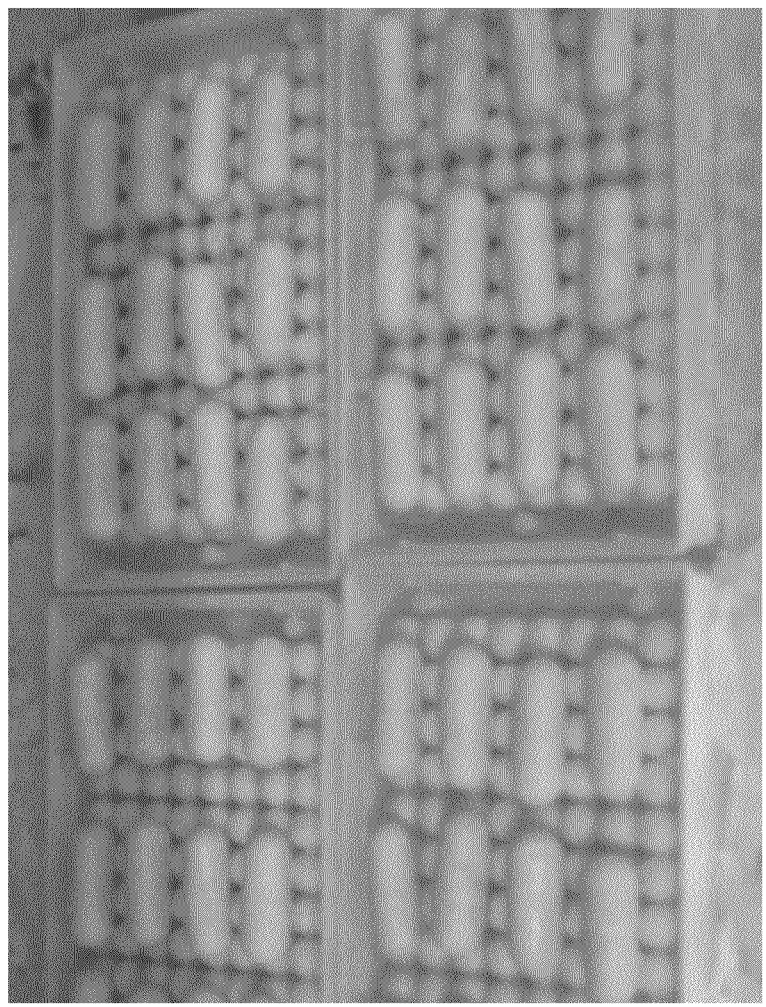

FIG. 6 is a photograph of ethyl cellulose coated particles. Each particle was coated with 15 ml or 13 ml of the polymer solution.

FIGS. 7A-B are photographs depicting particles coated with ethyl cellulose 8% or cellulose acetate 8% (in a time slides of weeks). FIG. 7A depict ethyl cellulose coated particles. The right particle is an empty gelatin capsule and the other particles are 1-4 weeks old ethyl cellulose coated particles. FIG. 7B depicts cellulose acetate coated capsules. The right particle is an empty gelatin capsule and the other particles are 1-3 weeks old cellulose acetate particles.

Figure 8:
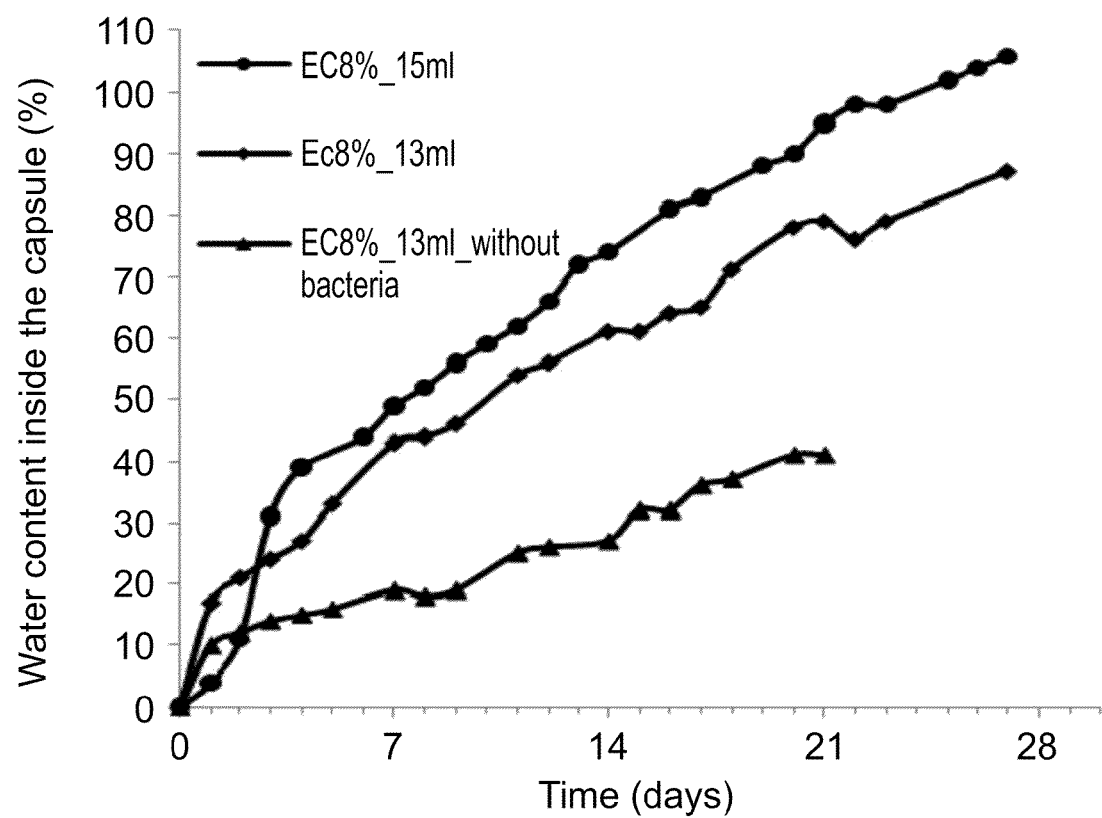

FIG. 8 is a graph depicting water penetration flow rate (% of total particle maximum weight after injecting water into the particles). Two types of 8% Ethyl cellulose (EC) coated particles were examined: one particle was coated with 15 ml and the other with 13 ml of the polymer solution (1.2 gr or 1.04 gr of ethyl cellulose and caster oil). The weights of the particles were 0.64 gr (15 ml coated particle) and 0.41 gr (13 ml coated particle). Particle water content of 30% was the point of particle activation. In the 8% Ethyl cellulose membrane particles, this was achieved after 72 h or 96 h for 15 ml (black circles) and 13 ml (black diamonds) coated particles, respectively. The particles that were coated with 15 ml of the polymeric solution reached maximum weight while the particles that were coated with 13 ml of the polymeric solution reached only 87% of the maximum particle weight. Particles which did not contain bacteria (black triangles) displayed a significant inhibition of water flow into the particle.

Figure 9:
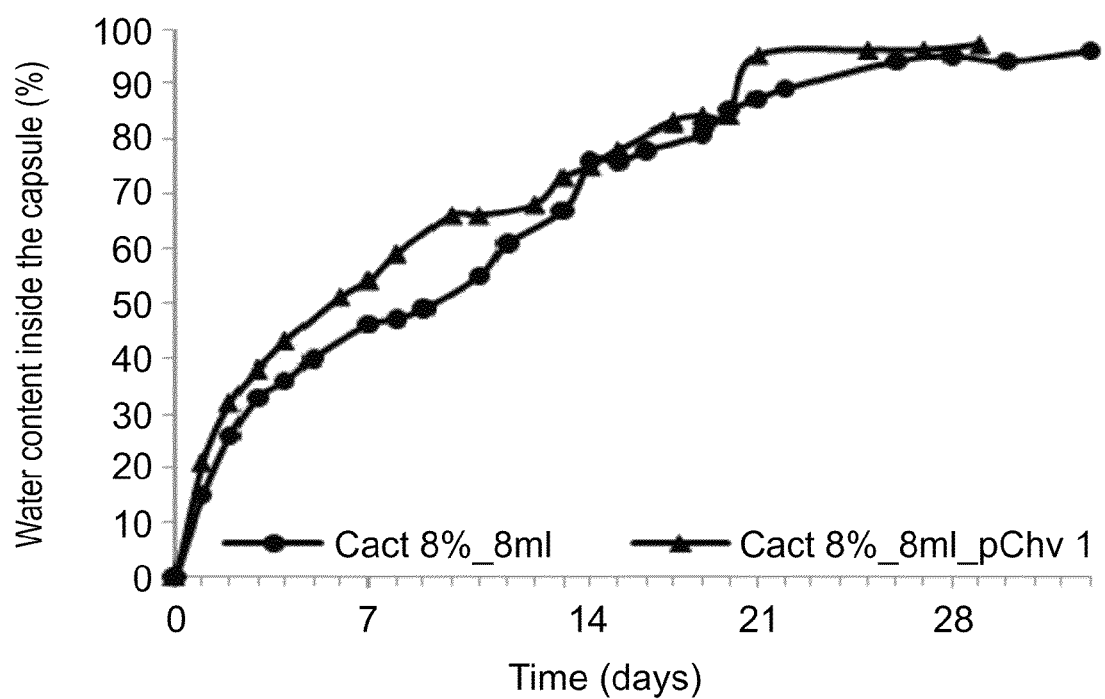

FIG. 9 is a graph depicting water flow rate into particles coated with 8% cellulose acetate and comprising different types of bacteria (E. coli TG1 and E. coli TG1 pChv1). The bacteria type had no influence on the water flow rate into the particles.

Figure 10:
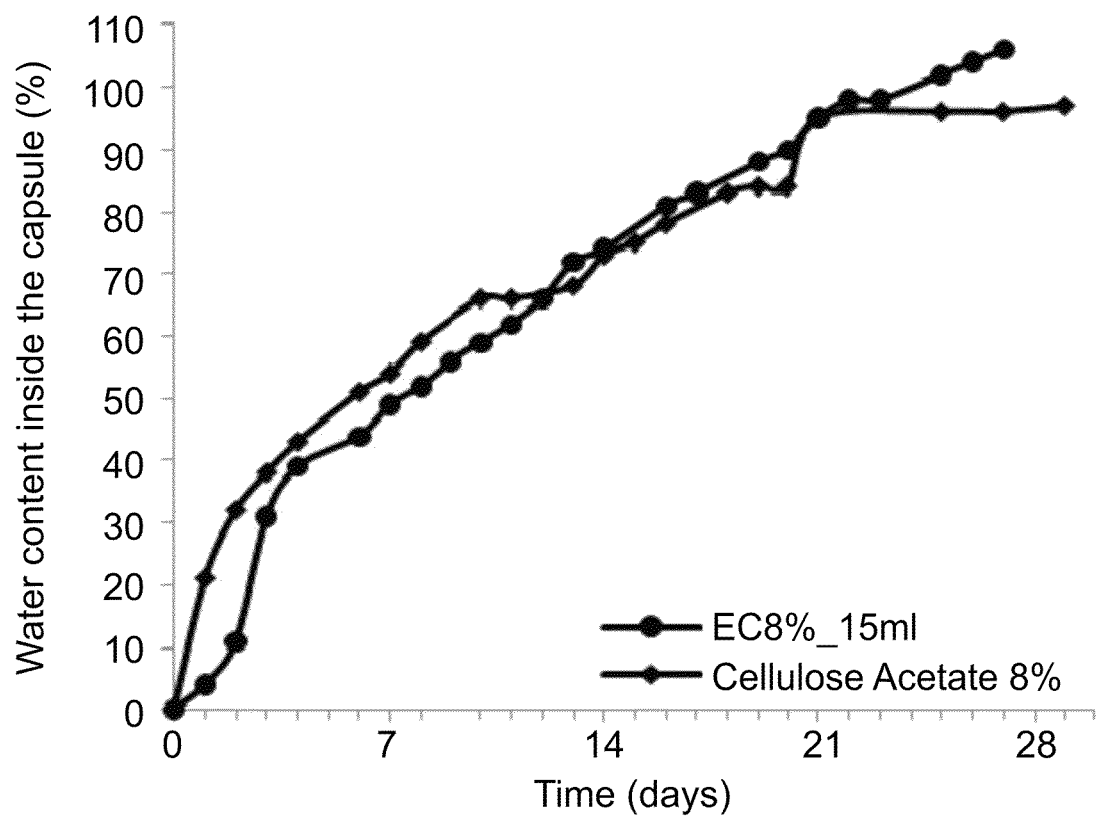

FIG. 10 is a graph depicting water flow rate into particles coated with either ethyl cellulose or cellulose acetate. The cellulose acetate particles displayed a faster activation point compared to the ethyl cellulose particles.

Figures 11A, 11B, 11C:
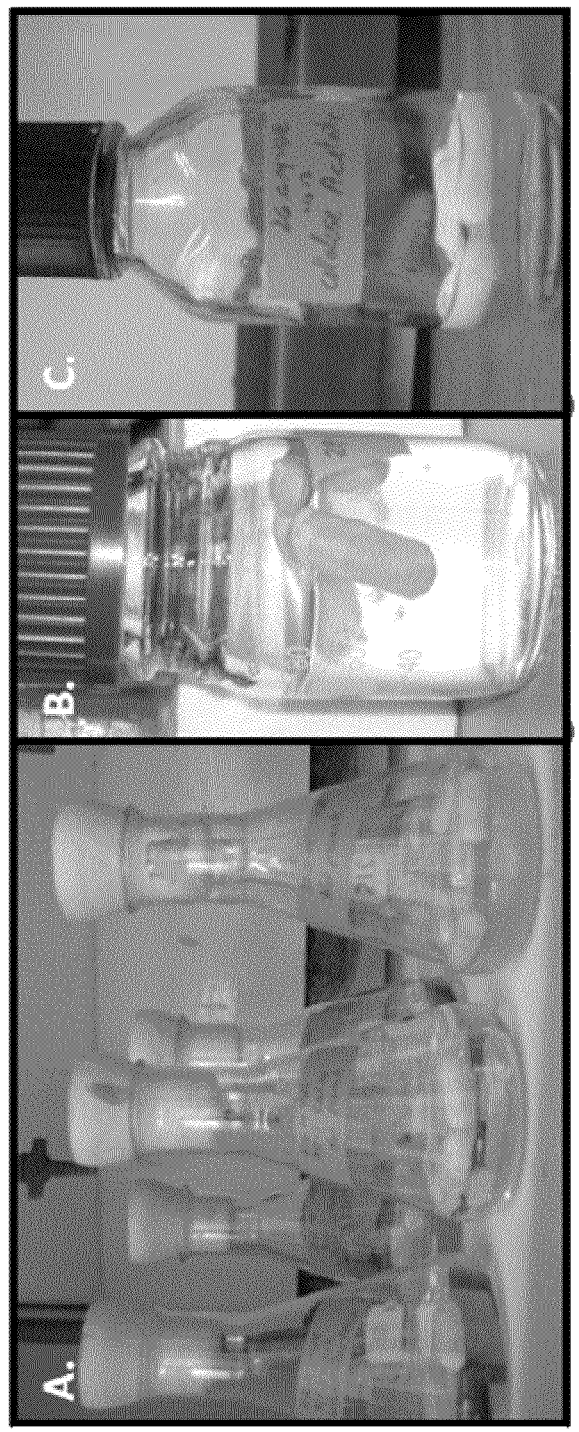

FIGS. 11A-C are photographs depicting activation and biocompatibility test systems. Each of the bottles or flasks used for testing contained saline and several particles (comprising different outer membrane coatings). The particles were maintained in the test systems for 5 weeks and viability was checked on a weekly basis. FIG. 11A shows flasks which contained 8% ethyl cellulose coated particles (13 ml); FIG. 11B shows a bottle which contained 8% ethyl cellulose coated particles (15 ml); and FIG. 11C shows a bottle which contained 8% cellulose acetate coated particles (8 ml).

Figure 12:
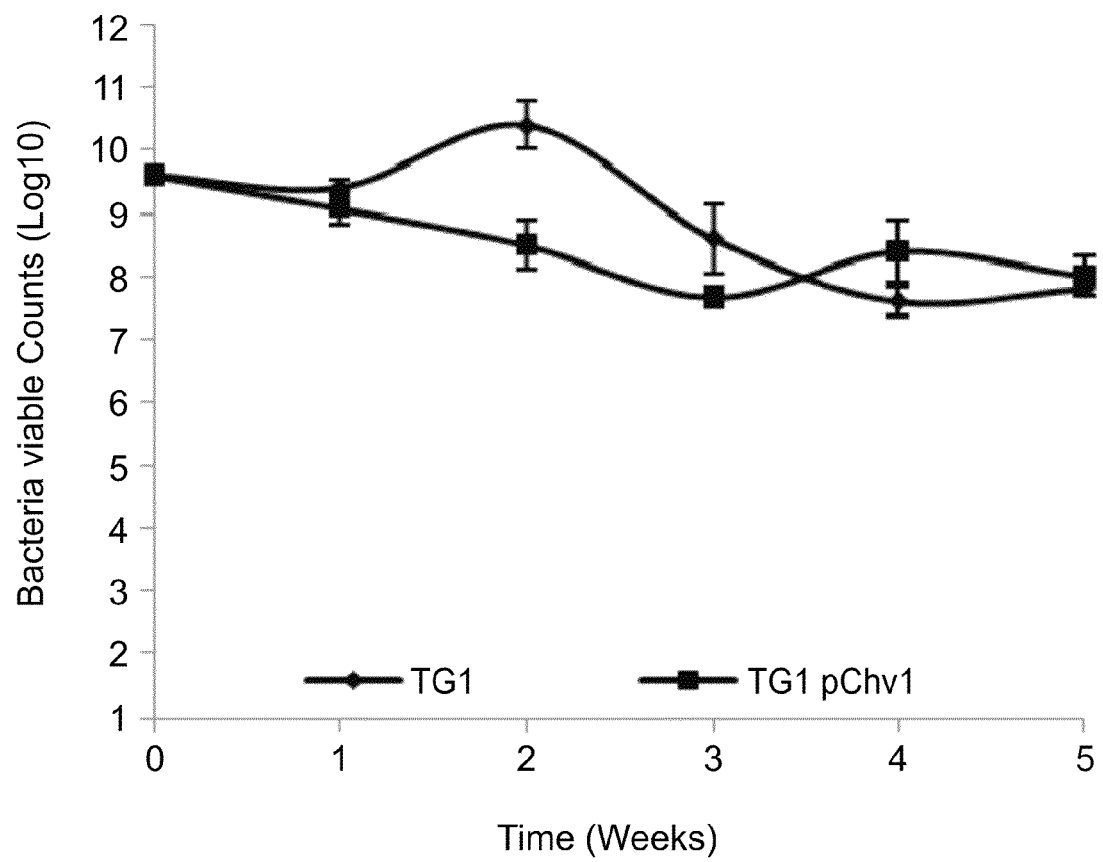

FIG. 12 is graph depicting bacteria viability (log 10 CFU/ml) within the activated cellulose acetate membrane particle. Liquid phase viability counts were carried out on a weekly basis. First, the liquid was pumped by using a syringe and a needle, next the obtained sample was serial diluted with saline. Two types of particles were tested: one which contained an E. coli TG1 culture and the other which contained E. coli TG1 pChv1. The outer membrane of both particles was identical and contained cellulose acetate 8% (each particle was sprayed with 8 ml of the polymer solution). Of note, the viability counts obtained from the two particles were similar. Furthermore, after 3 weeks of particle activation, a stable bacteria viability number was established (at an average of 8 log 10 CFU/ml) and after 5 weeks of particle activation, the bacteria concentration within the particle was high. The results represent bacteria viability of one representative particle (the bar represents the viability counts of each representative particle).

Figure 13:
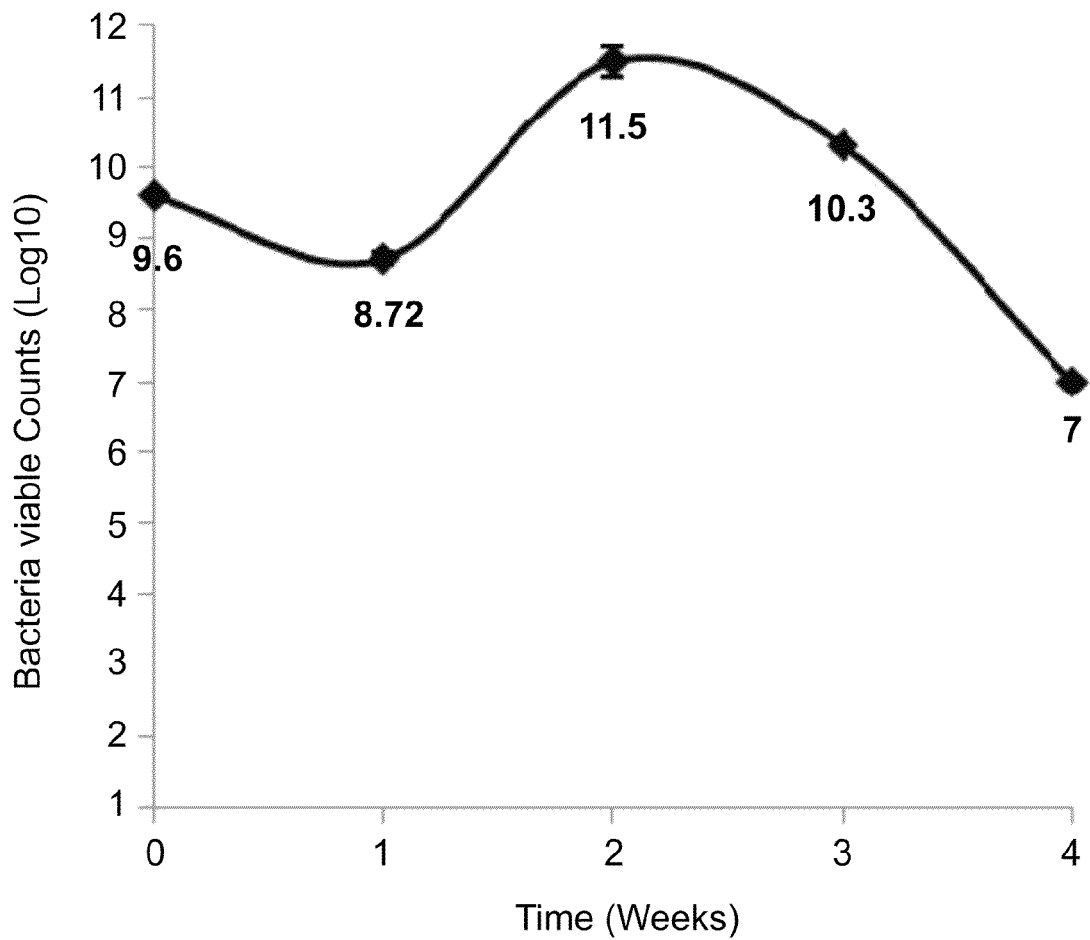

FIG. 13 is a graph depicting bacteria viability (log 10 CFU/ml) within the activated ethyl cellulose membrane particle. Liquid phase viability counts were carried out on a weekly basis. First, the liquid was pumped by using a syringe and a needle, next the obtained sample was serial diluted with saline. The outer membrane of the particle was coated with ethyl cellulose 8% (each particle was sprayed with 15 ml of the polymer solution). Particle biocompatibility was tested on a weekly basis for up to 4 weeks. Of note, a typical growth curve was observed. Thus, in the first week an environment culture adaptation of the bacterial culture was observed which was followed by logarithmic phase for more than 1 week. After 4 weeks, the culture concentration was 10,000,000 bacteria per 1 ml liquid.

Figure 14:
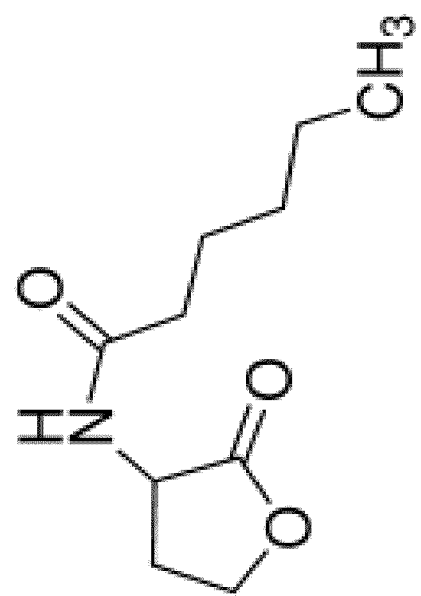

FIG. 14 is a diagram depicting the inducer homo-serine lactone. Homo-serine lactone was used as a model for molecule trafficking across the particle membrane.

Figure 15:
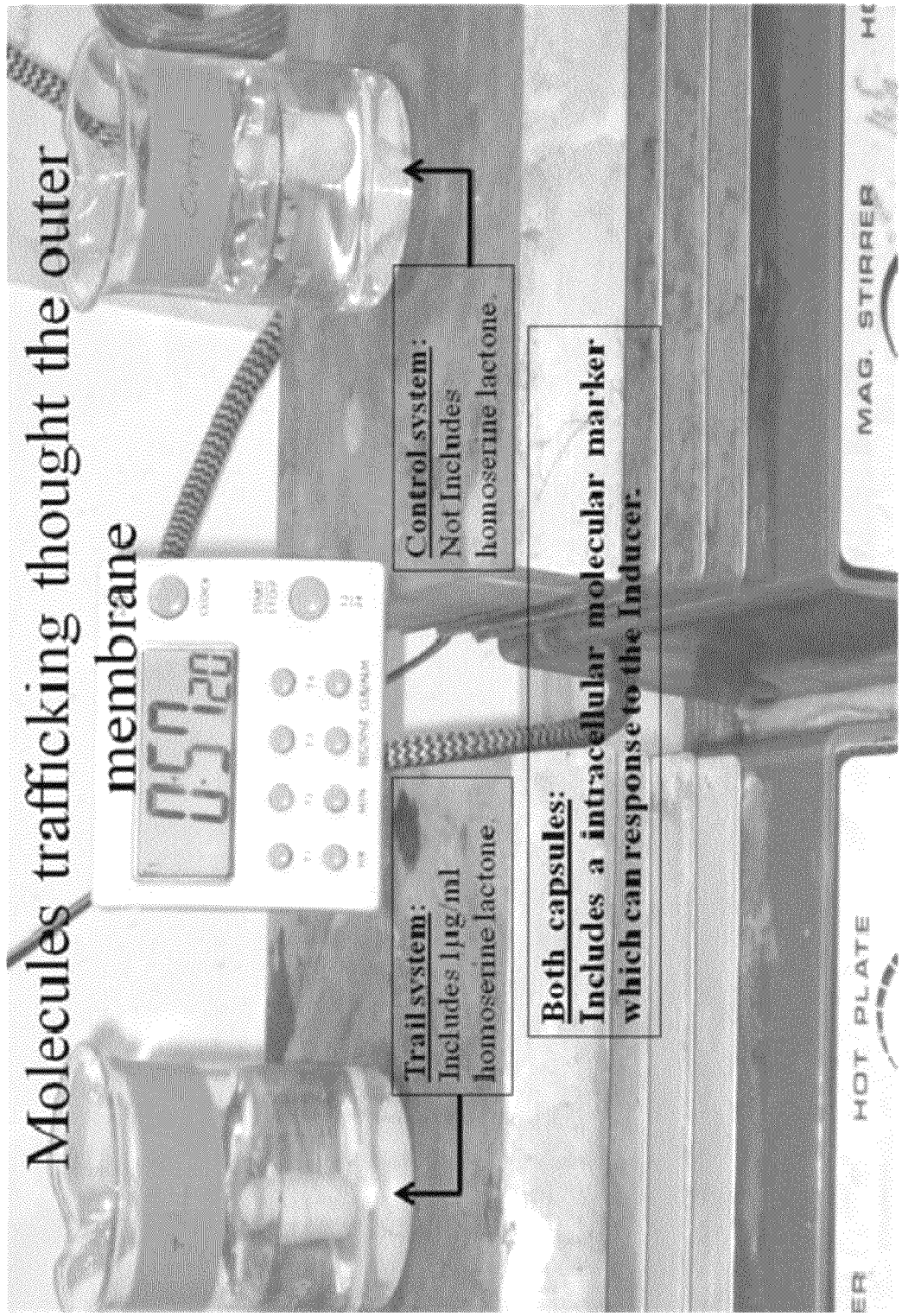

FIG. 15 is a photograph depicting molecule trafficking across the particle membrane (a validation experiment). The membrane permeability validation system included two systems: 1) the experimental system in which the inducer (1 μg/ml) was added to the particle medium (saline), and 2) the control system which did not contain the inducer in the particle medium. Each system contained one particle within a gently vortexed saline medium and in both systems the particles contained the same bacterial culture (E. coli TG1 pchv1, that was harboring the luciferase system). The particles were incubated inside each of the mediums for one hour prior to extraction of the particle inner medium (containing the planktonic bacterial culture) using a syringe with a needle. The sample collected was read in a Bio-Tek spectrophotometer (light detector sensitivity 125) on 96 wells plate. Light emission was observed and compared between the test culture, the control system and a blank medium (saline). The ratio between the results represents the intensity of the inducer transport.

Figure 16B:
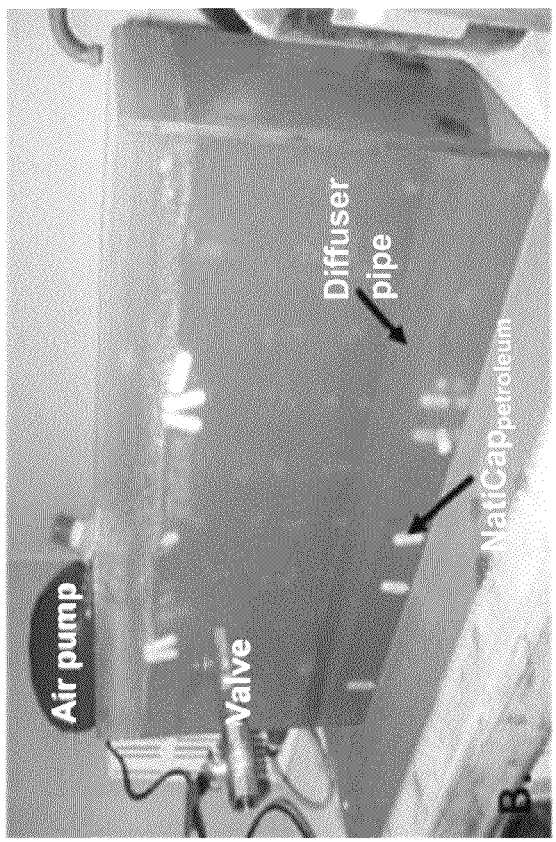
Figure 16C:
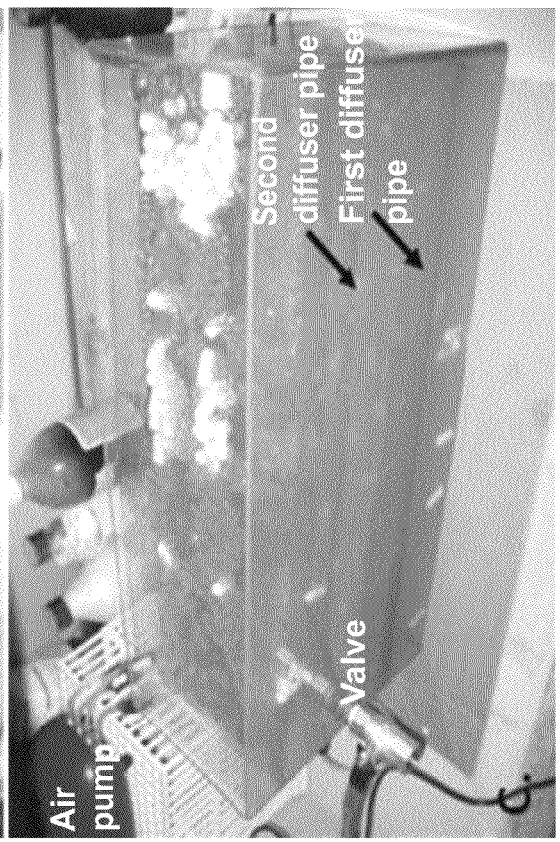
Figure 16A:
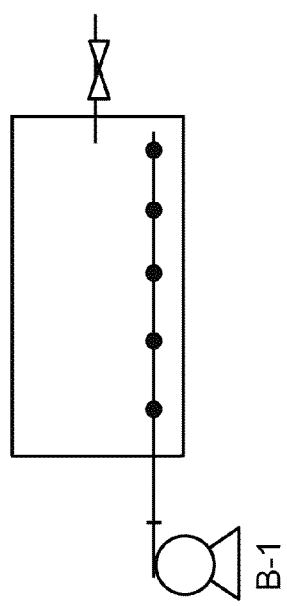

FIG. 16A is a diagram of the experimental system of petroleum wastewater (hydrocarbon biodegradation), depicted herein as NatiCap petroleum treatment.

FIGS. 16B-C are photographs depicting the test model. FIG. 16B shows a side view and FIG. 16C shows an upper view of the test system which includes the biological reactor, NatiCaps (75 particles), diffusers, samples valve and the air pump.

Figure 17:
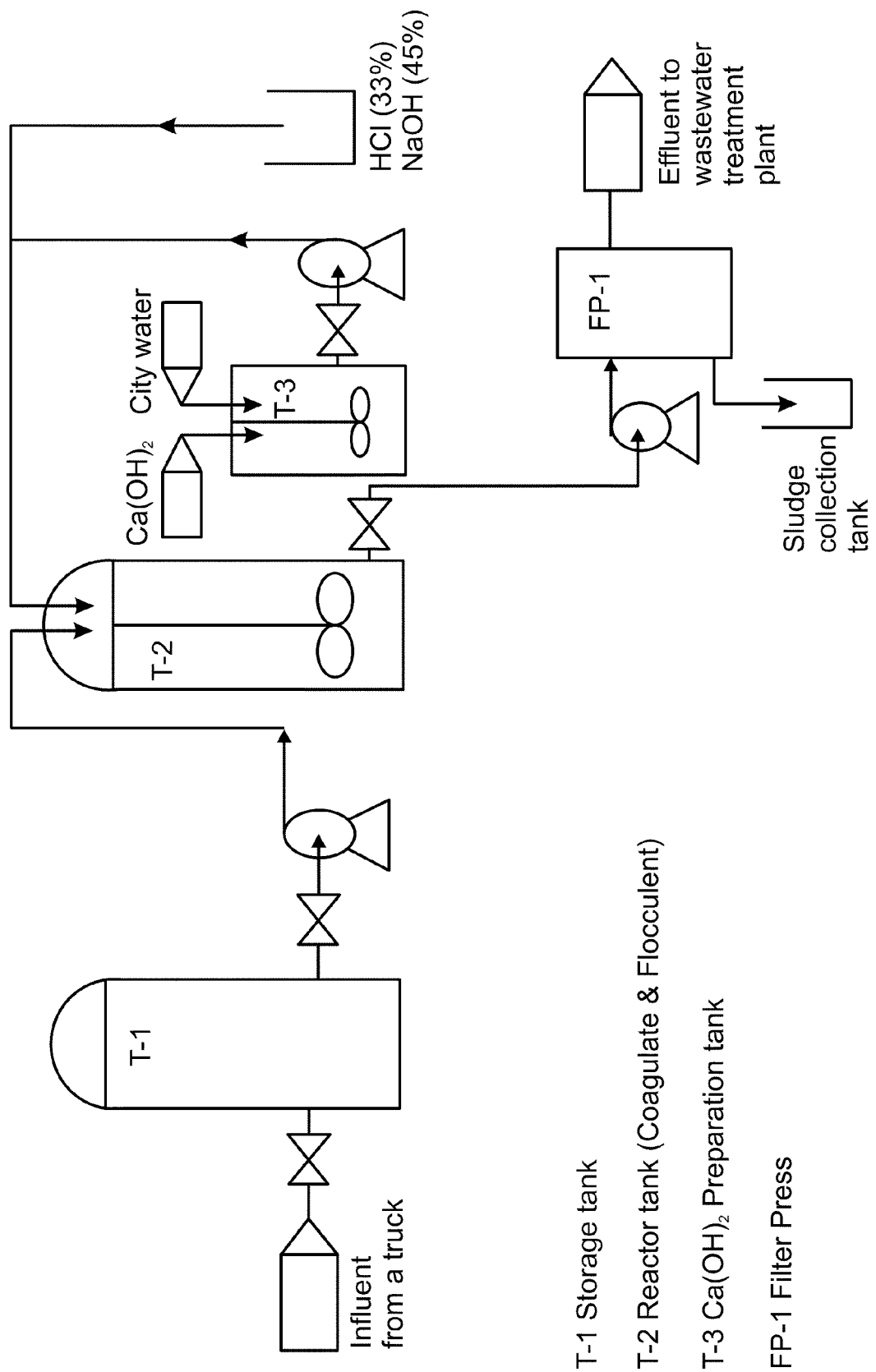

FIG. 17 is an illustration a typical a process flow draw (PFD) of heavy metals wastewater treatment (physicochemical technology in use for decontamination of petroleum wastewater and for heavy metals containing wastewater).

Figure 18:
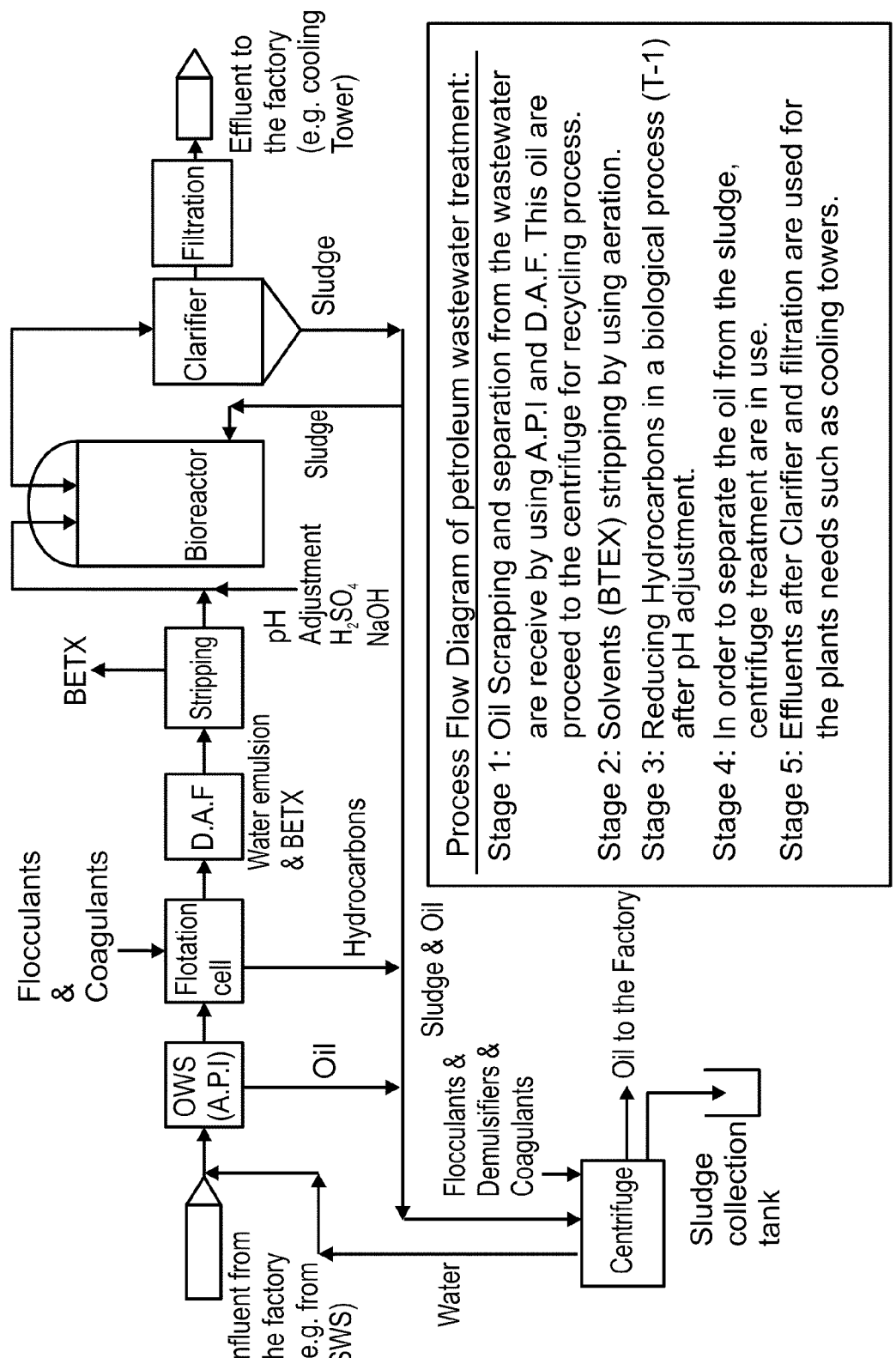

FIG. 18 is an illustration of a typical a process of refinery wastewater treatment (SWS—Sour Water Stripper).

Figure 19B:
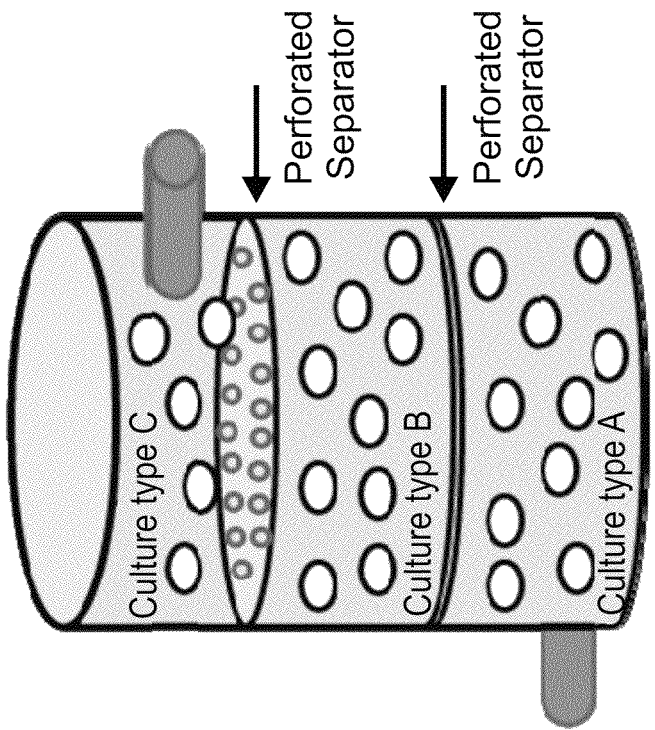
Figure 19A:
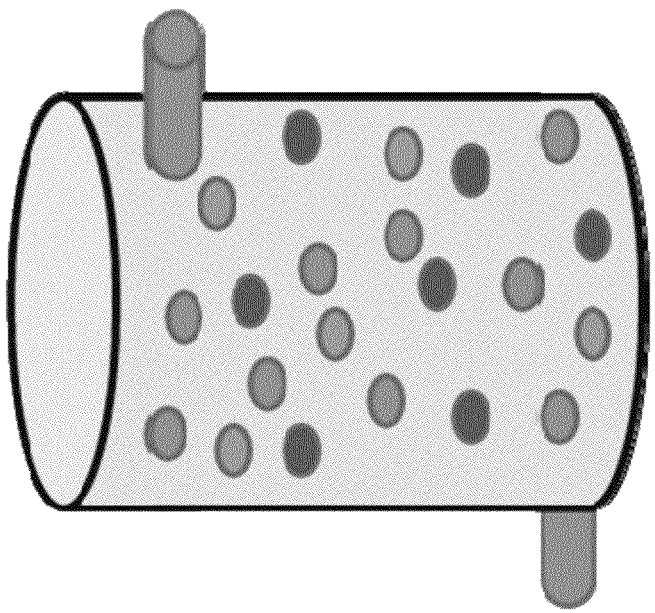

FIGS. 19A-B are illustrations of two methods of growing non-identical particles containing different microorganisms. FIG. 19A depicts culturing several non-identical particles in one host reactor. FIG. 19B depicts culturing the different non-identical particles in a host reactor which has internal chambers (separated by a perforated separator). The perforated separator pore size is selected smaller then the particle size. Each internal chamber contains one type of particles. The feeding liquid is circulated between the reactor chambers.

DESCRIPTION OF SPECIFIC EMBODIMENTS OF THE INVENTION

The present invention, in some embodiments thereof, relates to microorganism-comprising particles and, more particularly, but not exclusively, to the use of same for the removal of contaminants from water or soil, for treatment of diseases and for the production of pharmaceutical and cosmetic compositions.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventor has generated novel particles which comprise microorganisms within. The particles comprise an outer porous membrane which is selected such that it allows trafficking of molecules of a particular size (e.g. water molecules or proteins) while inhibiting trafficking of molecules of a larger size (e.g. microorganisms). The particles further comprise an inner core which supports microorganism growth and prosperity.

The present inventor demonstrated the use of the particles for wastewater treatment. Particles were generated which contained bacteria, inner cores, activated Carbon and degradation enzymes. These particles were placed in petroleum wastewater and were shown to significantly increase BOD (biological oxygen demand) and TSS (total suspended solids) levels (in both aerobic and anoxic stages) and to significantly decrease COD (chemical oxygen demand) levels (in the aerobic stages) indicating hydrocarbon degradation. Moreover, the particles exhibited good biocompatibility after 3 weeks within the petroleum wastewater and the necessary biomass within the particles developed within a short period (within 3 days). The present teachings portray the use of the particles for removal of contaminants, such as from waste water or soil.

The present inventor further demonstrated, using a luciferase test system, that molecules of certain size can be transported back and forth through the particle outer membrane. More specifically, the present inventor generated particles containing genetically transformed bacteria (i.e. comprising a plasmid that contained the entire luciferase system). The system inducer (i.e. Homo serine lactone—C10 hydrocarbon), was added to the medium in which the particle was placed and upon penetration of the particle (and contact with the bacteria), transcription of the plasmid was induced. These results indicate that the particles comprise pores of a size which allow the passage of the inducer from the medium into the particle.

Hence, the present teachings suggest the use of the particles for production of desired molecules (e.g. recombinant polypeptides). Such molecules may be used in pharmaceutical or cosmetic compositions. Genetically transformed microorganisms (e.g. bacteria or yeast) capable of synthesizing the desired molecules (e.g. polypeptides), may be generated and placed within the particles. The pore size of the outer membrane can be selected such that the recombinant polypeptide exits the particle into the surrounding medium, but the genetically engineered bacteria cannot. This allows for easy extraction and purification of the molecules thereby increasing efficiency and overall yield. Furthermore, since the particles may be used in production batches working in continuous process modes, the time interval between the production batches may be reduced.

Thus, according to one aspect of the present invention there is provided a particle comprising: (i) at least one inner core which comprises a solid matrix of nutrients for microorganism growth, (ii) an inner membrane being fabricated from a water-soluble polymer, the inner membrane surrounding the inner core and a population of dried microorganisms, and (iii) an outer porous membrane surrounding the inner membrane, the outer porous membrane being insoluble in water.

The term "particle" as used herein refers to an enclosed structure (e.g. capsule). The particle of the present invention may be of various shapes and sizes depending on the intended use of the particle (described in further detail below). Thus, the particle may be about 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 25 cm, 30 cm, 35 cm or 40 cm in length.

The term "microorganism" as used herein refers to an organism (e.g. single cell organism) which is only visible using a microscope. The organism of the present invention can be a eukaryotic organism (e.g., protozoa, algae or fungi for example yeast) or a prokaryotic organism (e.g., bacteria or archaea). The microorganisms of the present invention may be in any cellular environment, such as for example, in a biofilm, as isolated cells or as a cell suspension.

Exemplary bacteria which may be comprised in the particle of the present invention include gram positive bacteria and gram negative bacteria (see also list in Table 1, below).

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abscessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Sarcina lutea, Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B streptococcus), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis.*

The term "Gram-negative bacteria" as used herein refer to bacteria characterized by the presence of a double membrane surrounding each bacterial cell. Representative Gram-negative bacteria include *Acinetobacter calcoaceticus, Acinetobacter baumannii, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella pneumoniae, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Shigella sonnei, Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis.*

The term "fungi" as used herein refers to the heterotrophic organisms characterized by the presence of a chitinous cell wall, and in the majority of species, filamentous growth as multicellular hyphae. Representative fungi which may be comprised in the particle of the present invention include *Candida albicans, Saccharomyces cerevisiae, Candida glabrata, Candida parapsilosis* and *Candida dubliniensis* (see also list in Table 1, below).

The term "yeast" as used herein refers to the eukaryotic micro-organisms classified in the kingdom Fungi. Representative yeast which may be comprised in the particle of the present invention include *Yarrowia lipolytica, Saccharomyces cerevisiae, Candida albicans, Rhodotorula rubra, Torulopsis* and *Trichosporon cutaneum* (see also list in Table 1, below).

The term "algae" as used herein refers to the simple, typically autotrophic eukaryotic organisms. Representative algae which may be comprised in the particle of the present invention include *Chlorella, Chlamdomonas, Chaetoceros, Spirolina, Dunaliella* and *Porphyridium*.

It will be appreciated that selection of the microorganisms used will be determined according to the intended use of the particle (described in further detail below). For example, if the particle is used for petroleum wastewater treatment the microorganisms used may be selected from the list detailed in Table 1, below.

TABLE 1

List of microorganisms for use in petroleum wastewater treatment

| Yeast | Fungi | Bacterial |
|---|---|---|
| 1. *Sporobolomyces*. | 1. *Penicillium*. | 1. *Bacillus megaterium* (ATCC 14581). |
| 2. *Trichosporon*. | 2. *Cuaninghamella*. | 2. *Bacillus brevis* (ATCC 8246). |
| | 3. *Verticillium*. | 3. *Bacillus subtilis*. |
| | 4. Rhodosporiodium. | 4. *Bacillus punillis*. |
| | 6. *Brevibacterium*. | 6. *Bacillus licheniformis*. |
| | 7. *Corynebacterium*. | 7. *Escherichia coli* (ATCC 33456). |
| | 5. *Bacillus firmus*. | 8. *Entrobacter aerogenes* |
| | | 9. *Pseudomonas putida* spp. (ATCC 12633). |
| | | 10. *Pseudomonas stutzeri* AN10. |
| | | 11. *Pseudomonas alcaligenes*. |
| | | 12. *Micrococcus luteus* (ATCC 4698). |
| | | 13. *Micrococcus lylae* |
| | | 14. *Stenotrophomonas multophila* (ATCC 12714, 13270, 14535, 17666). |
| | | 15. *Acinetobacter faecalis*. |
| | | 16. *Acinetobacter baumannii* (ATCC19606). |
| | | 17. *Arthrobater* spp. |
| | | 18. *Achromobacter* spp. |
| | | 19. *Nocardia asteruides* (ATCC10904). |
| | | 20. *Nocardia* spp. (ATCC12288). |
| | | 21. *Rhodotrula* spp. |
| | | 22. *Beauveria bassiana*. |
| | | 23. *Burkholderia capasia*. |
| | | 24. *Morthierilla* spp. |
| | | 25. *Flavobacterium* spp. |

According to one embodiment, the microorganisms comprised in the particle are a homogenous population.

According to another embodiment, the microorganisms comprised in the particle are a heterogeneous population.

Typically, the microorganisms of the present invention are dried (e.g. in a powder form) prior to encapsulation thereof.

Any suitable drying technology such as freeze-drying, spray drying, refractive windows drying (described for example. in U.S. Application No. 20070122397) drying under reduced pressure (described for example. in PCT Publication No. WO/2001/036590) may be used so long as the microorganisms are capable of propagating following activation (i.e. remain viable).

For example, freeze-drying may be carried out as described in detail in Example 1 of the Examples section which follows. In short, microorganisms (e.g. bacteria) are grown for a suitable length of time (e.g. overnight) in growth medium. The bacteria is collected (e.g. by centrifugation) and suspended (e.g. in PBS solution). The suspended culture is collected (e.g. by centrifuged) and suspended (e.g. in ice cold PBS comprising 5% sucrose). The culture is incubated (e.g. at room temperature, 22° C.) for a short period of time (e.g. 20 minutes) and then incubated for several days (e.g. 48-72 h) at a freezing temperature (e.g. −80° C.). Finally, the culture is freeze-dried for a few days (e.g. 52 h) using a protective freeze agent (e.g. sucrose) and stored at room temperature (e.g. inside a dissector).

The present invention contemplates introduction of at least about $10^6$, $10^7$, $10^8$, $10^9$, $10^{10}$, $10^{11}$ or $10^{12}$ microorganisms/ml into the particle. It will be appreciated that during the life span of the particle, the microorganism levels may increase or decrease (especially after activation of the particle as described below).

In order to support microorganism growth, the particle of this aspect of the present invention comprises a solid matrix of nutrients (also referred to herein, as the inner core).

As used herein the term "solid matrix" refers to any solid material which comprises a microorganism (e.g. bacterial) growth supportive capacity. Typically the inner core contains sufficient nutrients to facilitate viability and growth of the microorganisms contained within the particle for at least 5 days, more preferably 10 days, more preferably 20 days, 30 days or more.

Particular compositions (e.g. matrixes and nutrients) suitable for use in growing microorganisms are well known in the art (see for example, Shijun Liu and Laurie Usinger, For example, the inner core may comprise an agar including e.g. Luria Agar (LA), LB (Luria Bertani) Agar, MacConkey Agar, Miller's LB Agar, Blood agar, Chocolate agar, Hektoen enteric agar (HE), mannitol salt agar (MSA) and the like, or gelatin.

According to the present teachings, the solid matrix may comprise additional nutrients which support microorganism growth and/or which augment the microorganism activity (e.g. decontaminating activity). Thus, the inner core may comprise, for example, a source of amino acids and nitrogen (e.g., beef, yeast extract, tryptone), a sugar or carbon source (e.g. glucose), water, various salts (e.g. NaCl), essential elements (e.g. iron, magnesium, nitrogen, phosphorus, and sulfur), other compounds (e.g. lactate) and enzymes (e.g. degradation enzymes). The inner core may additionally comprise any nutrient needed for the microorganism growth and prosperity.

According to one embodiment, the inner core is dried prior to encapsulation thereof so as to prevent unwanted activation of the microorganisms. The inner core may be dried according to any suitable drying method known to one of ordinary skill in the art. Thus, for example, the inner core may be air-dried, dried in biological hood or vacuum-dried.

The inner core may be coated with a control release polymer such as a sustained release polymer which may control the rate of release of the nutrients from the inner core. Such polymers may include, without being limited to, a polyvinyl acetate (PVA)-based material, Kollidon SR (PVA/PVP matrix), Kollicoat SR 30D (30% aqueous dispersion of polyvinyl acetate stabilized with polyvinyl pyrrolidone), chitozan, polylactic-co-glycolic acid (PLGA) or PLGA with Polylactic acid (PLA).

It will be appreciated that the particle of the present invention comprises an inner membrane which encapsulates the inner core and the dried microorganisms. The inner membrane of the present invention is typically fabricated from a water-soluble polymer.

As used herein, the phrase "water-soluble polymer" refers to a polymer that dissolves in an aqueous medium after at least one week of incubation therein, more preferably after 5 day incubation and even more preferably after 1 day incubation.

The water-soluble polymer may be a natural water-soluble polymer or a synthetic water-soluble polymer. Examples of such include, but are not limited to, gelatin, agar, polyethylene glycol, acrylic acid polymers, polysaccharide, polysaccharide gum and sodium alginate. It will be appreciated that the inner membrane may be fabricated from one polymer, from two polymers, from three polymers or from several polymers as can be determined by one of ordinary skill in the art.

The thickness of the inner membrane may be from about 1 μm to about 500 μm.

According to a specific embodiment, the inner membrane is fabricated from gelatin.

It will be appreciated that additional elements may be incorporated into the inner membrane. These may include glass or polymer beads, activated carbon granules, activated carbon chips, enzymes and nutrients (see list hereinabove).

The material of the inner membrane and components comprised therein may be selected to support biofilm formation.

As used herein the term "biofilm" refers to is an aggregate of microorganisms in which cells adhere to each other and/or to a surface. These adherent cells are frequently embedded within a self-produced matrix of extracellular polymeric substance (EPS) in which microorganisms are dispersed and/or form colonies. The biofilm typically is made of polysaccharides and other macromolecules.

Biofilm formation may occur, for example, on the surface of the inner core (e.g. on the solid matrix), on the inside surface of the inner membrane (e.g. on the inner surface of the gelatin particle), as well as on the additional components (e.g. on the surface of the glass beads or on the surface of the carbon granules/chips).

Thus the number of additional components may be selected according to the level of biofilm formation required.

In addition, the number of additional components may be selected according to the weight/buoyancy required.

As mentioned, the particle of the present invention further comprises an outer porous membrane surrounding the inner membrane.

The outer porous membrane is typically water-insoluble (i.e. the pore size of the membrane should not change following incubation in water). In addition, the porous membrane needs to withstand harsh unstable environments (e.g. pH variations).

In order to prevent clogging of the pores, the outer porous membrane may be fabricated from a material that is resistant to biofilm formation.

There is wide variety of polymers that may be used to fabricate the porous outer membrane according to this aspect of the present invention. Below is a list of such polymers (see Table 2 for possible vendors of same): PVAL (polyvinyl-alcohol), Polyethersulfone (PES), Cellulose Acetate, Cellulose Nitrate, Ethyl Cellulose, Nitrocellulose Mixed Esters, Polycarbonate film, Nylon, PVDF (poly(vinylidene fluoride)), Polysulfone, PVOH, polyacrylamide, Poly(4-vinyl-N-alkylpyridinium bromide), poly(methacryloyloxydodecylpyridinium bromide, N-alkylated poly(4-vinyl pyridine), Poly (vinyl-N-hexylpyridinium), poly(N-alkyl vinylpyridine), poly(N-alkyl ethylene imine), poly(4-vinyl-N-alkylpyridinium bromide), poly(4-vinyl-N-hexylpyridinium bromide), Poly (1-(chloromethyl).sub.4-vinylbenzene, Poly (Dimethyloctyl[4-vinylphenyl]methylammonium chloride), Poly (Dimethyldodecyl[4-vinylphenyl]methylammonium chloride), Poly (Dimethyltetradecyll[4-vinylphenyl]methylammonium chloride), 50:50 Poly (1-Chloromethyl)-4-vinylbenzene): Poly (Dimethyldodecyl[4-vinyl-phenyl]methylammonium chloride), 50:50 Poly (1-Chloromethyl)-4-vinylbenzene): Poly (Dimethyloctyll[4-vinylphenyl] methylammonium chloride), 50:50 Poly (Dimethyldodecyll [4-vinylphenyl]methylammonium chloride): Poly (Dimethyloctyll[4-vinylphenyl]methylammonium chloride), Poly (Tributyl-[4-vinylphenyl]methylphosphonium chloride) and Poly (Trioctyl-[4-vinylphenyl]methylphosphonium chloride).

TABLE 2

Porous outer membrane polymers and vendors

| Manufacture companies | Raw materials |
| --- | --- |
| Kuraray, Shanxi Sanwei Group | PVAL (polyvinyl-alcohol) |
| Sterlitech, Sigma-aldrich, General Electric Osmonics Labstore | Polyethersulfone (PES) |
| Sterlitech, General Electric | Cellulose Acetate |
| Osmonics Labstore | Cellulose Nitrate |
|  | Ethyl cellulose |
| Sterlitech, General Electric Osmonics Labstore | Nitrocellulose Mixed Esters |
| Sterlitech | Polycarbonate film |
| Sterlitech | Nylon |
|  | PVDF(poly(vinylidene fluoride)) |
|  | Polysulfone |

According to a specific embodiment the outer porous membrane is fabricated from Cellulose Acetate.

According to a specific embodiment the outer porous membrane is fabricated from Ethyl Cellulose.

The outer porous membrane of the particle may be fabricated uniformly of a single polymer, co-polymer or blend thereof. It is possible to form a porous membrane from a plurality of different polymers. There are no particular limitations to the number or arrangement of polymers used in forming the porous membrane. Any combination which is water-insoluble and enables formation of pores may be used. It is possible, for example, to apply polymers sequentially.

As mentioned, the pore size of the outer membrane is selected such that it allows trafficking of molecules of a particular size (e.g. water or proteins) while inhibiting trafficking of larger molecules (e.g. microorganisms). Thus, according to an embodiment of the present invention, the pore of the porous membrane is less than 0.95 μM, 0.90 μM, 0.85 μM, less than 0.80 μM, less than 0.75 μM, less than 0.70 μM, less than 0.65 μM, less than 0.60 μM, less than 0.55 μM or less than 0.50 μM.

It will be appreciated that any method known in the art may be used to generate the particle of the present invention.

For example, according to the present teachings, the particle may be generated by inserting at least one inner core (i.e. solid matrix of nutrients) into the inner membrane. Any number of inner cores may be placed in the inner membrane as to support sustained microbial growth and proliferation. For example, 2 inner cores, 3 inner cores, 4 inner cores, 5 inner cores or more may be placed within the inner membrane. One of ordinary skill in the art will be able to determine the number of inner cores needed according to the intended use of the particle (described in further detail below).

It will be appreciated that for particular applications the particle does not have to comprise a solid matrix of nutrients. However, it is anticipated that according to this embodiment other elements are incorporated inside the inner membrane to enhance biofilm formation (e.g. the glass beads).

According to one embodiment, the inner membrane comprises dried nutrients in a powder form According to another embodiment, the particle does not comprise nutrients, but relies on nutrients from the exterior culture medium. This may be particularly relevant for the application for synthesizing a molecule of interest, wherein the synthesis is effected in a reactor comprising a culture medium. In such circumstances, the nutrients required to support microorganism growth and prosperity may be supplied in the exterior culture medium (e.g. in the bioreactor).

Other components may also be added into the inner membrane such as the dried organisms (e.g. bacteria) and any additional components needed (e.g. glass beads, carbon granules/chips).

Once all the necessary components are added to the inner membrane, it is coated with a water-insoluble porous membrane (described in detail above). Coating the particle may be carried out by any method known in the art, as for example, by spraying, dripping, immersing etc. The thickness of the outer membrane may be from about 1 µm to about 1000 µm. Moreover, the particle may be spayed several times on each side (e.g. 3-4 times) as needed to obtain the required thickness.

The particles for any of the below described applications may be pre-activated prior to use so as to transform the microorganisms comprised therein from a non-proliferating state to a proliferating state). Activating the population of microorganisms within the particle is effected by first contacting the particle with a liquid under conditions that allow the liquid to penetrate the outer porous membrane and wet the dried microorganisms According to one embodiment, the particle is contacted with the liquid for a period of several hours to several days. According to a specific embodiment, the particle is contacted with the liquid for a period of about 24 to 96 hours.

The liquid substance which may be used to activate the microorganism may comprise any aqueous material, as for example, water, saline or medium (e.g. cell growth medium) which is non-toxic to the microorganisms within. It will be appreciated that a mixture of saline or water or buffer with wastewater may be used or alternatively the particles may be gradually exposed to wastewater during activation thereof (e.g. by increasing the concentration of the wastewater within the saline).

Following activation of the microorganisms, the particles may be relocated to a location of interest according to their intended use (e.g. into soil, wastewater etc.). It will be appreciated that the particles of the present invention may also be used without pre-activation.

The particles of the present invention are contemplated for varied uses, as described herein below.

Thus, according to one aspect of the present invention, the particles are used for purifying water.

According to the present teachings, purifying water is effected by contacting the water with at least one particle under conditions that allow the microorganisms to decontaminate the water.

The temperature under which the decontamination procedure is carried out is selected such that it does not affect the viability of the microorganisms.

Use of the particles is effective for the length of time that the microorganisms remain viable and are capable of carrying out the decontamination procedure. Once the microorganisms are no longer effective, the particles may be removed and depending on the level of the contamination additional particles may be added.

As used herein the phrase "purifying water", refers to the process of removing undesirable chemicals, materials, and biological contaminants from the water. Water purification may be designed for a variety of purposes, including for drinking or for meeting the requirements of medical, pharmacology, agriculture, chemical and industrial applications.

As used herein the phrase "decontaminate water" refers to the process of removal of poisonous or otherwise harmful substances, such as noxious chemicals, from the water.

Preferably, the water is decontaminated by at least about 20%, 30%, 40%, 50%, 60%, 70%, 80%, 90% or preferably by about 100%.

It will be appreciated that any water source in need thereof may be purified according to the present teachings, including, but not limited to, drinking water, waste water (e.g. petroleum wastewater, heavy metal wastewater, municipal wastewater, industrial wastewater, agricultural wastewater, domestic wastewater), bathing water (e.g. pool, bath water) or large water source (e.g. ocean, river, pond). The water may be fresh waster or salt water.

Any water contamination may be treated according to the present teachings including, but not limited to, the removal of chemicals including petroleum hydrocarbons, phosphorous compounds, nitrogen compounds, pesticides, sulphides, phosphates, cyanides, lead and other heavy metals, organic compounds including solvents (e.g. BTEX-benzene, toluene, ethylbenzene, xylenes and organic solvents), phenols, pharmaceutical mixture waste, detergents, organometallo constituents (e.g. vanadium and nickel), and oil (e.g. vegetable oil, mineral oil, oil spills, floating oil, dispersed oil, dissolved oil).

Municipal enhancement treatment after wastewater treatment may also be carried out according to the present teachings. Thus, the particles may be used to degrade and accumulate difficult biodegradative organic matter and to reduce the concentration level of heavy metals, phosphorus, nitrogen and the like.

The present teachings may be combined with any other water purifying methods including physical (e.g. filtration and sedimentation), chemical (e.g. flocculation and chlorination and the use of electromagnetic radiation such as ultraviolet light) or biological treatment processes (e.g. slow sand filters or activated sludge).

Thus, the particles of the present invention may be incorporated with presently known systems as for example in physicochemical procedures of heavy metal treatment (FIG. 17) and sour water strippers (FIG. 18).

For example, in the physicochemical procedure [process flow draw (PFD) presented in FIG. 17], the particles may be added to the reactor number 2 (T-2) in which sedimentation of heavy metal takes place. In order to confirm to the use of particles, the system may need to be adjusted, as for example, by the replacement of the reactor mixer with diffusers.

In refinery wastewater treatment (SWS—Sour Water Stripper, presented in FIG. 18), the particles may be added to the bioreactor.

It will be appreciated that when the particles of the present invention are combined with other decontamination systems, different parameters including e.g. pH, chemicals, oxidizers, metals, coagulants (e.g. Aluminum sulfate, Aluminum Chloro Hydrate, Ferric chloride, Ferric/ferrous sulfate) and flocculants (e.g. FL-neg, FL-2, FL-pos) may be adjusted in the wastewater to enable optimal microorganism viability and activity.

The particles of the present invention can be targeted to a specific area. Thus, if for example a water surface needs to be decontaminated (e.g. for treatment of an oil spill or other floating hazardous substances) then the particles may be generated in a manner such that they float (e.g. may be generated without the addition of glass beads). Alternatively, if an area below the water surface needs to be decontaminated (e.g. petroleum or natural gas underground storage tanks), then the particles may be generated such that they do not float thereby enabling them to target the contamination at particular depths below the water surface.

The present teachings further contemplate the use of the particles for treating soil contamination.

As used herein the term "soil contamination" refers to the presence of xenobiotic (man-made) chemicals or other alteration in the natural soil environment, such as organic compounds, metals and oils.

It will be appreciated that any soil contamination may be treated according to the present teachings including, but not limited to, rupture of underground storage tanks, application of pesticides, percolation of contaminated surface water to subsurface strata, oil and fuel dumping, leaching of wastes from landfills or direct discharge of industrial wastes to the soil. These include decontamination of chemicals including petroleum hydrocarbons, solvents, pesticides, lead and other heavy metals.

Preferably, the soil is decontaminated by at least about 20%, 30%, 40%, 50%, 60%, 70%, 80%, 90% or preferably by about 100%.

It will be appreciated that prior to treating soil contamination, the particles are activated in a liquid substance (as described in detail above).

For both soil and water decontamination one type of particle (i.e. comprising identical microorganisms) may be used. Alternatively, two or more non-identical particles comprising different populations of microorganisms may be used. These particles may be used concomitantly or subsequent to each other (e.g. at the same time or at different times as needed).

For soil and water decontamination, the particles may comprise microorganisms which have been isolated from the contaminated area. Thus, microorganisms (e.g. bacteria) may be obtained from the desired decontaminated area, isolated and dried prior to encapsulation thereof in the particles. The microorganism may be obtained from commercial companies as for example from USAbioproducts (Type 4), Acron Biotechnical Corporation (ENSPOR S1), Advanced BioTech (Bioworld), One Biotechnology (BioOne®), Natural Environmental Systems, LLC (NE8000PH, NE2000MUN), A&V Envirotech (Bacti-Bio 1100G) or BPC (BPC-ACT™).

Determination of the microorganism population or populations to be used can be determined by one of ordinary skill in the art. An exemplary list of microorganisms and their possible applications is listed in Table 3, below.

TABLE 3

| Reference | Reaction type | Application | Microorganisms |
|---|---|---|---|
| Heavy metal absorption and accumulation | | | |
| Luque-Almagro et al. | Aerobic | Alkaline metal-cyanid complex (nitrogen source) Cyanid degradation and metal absorption | 1. *Pseudomonas fluroscens* 2. *P. pseudoalcaligenes* CECT5344 |
| Laddaga, R. A., et al. | | Cadmium absorption via nonspecific cation transporter | *Bacillus subtilis* |
| | Aerobic or anaerobic | Metal ($Cu^{+2}$) fixation by bacterial cell wall | *Bacillus licheniformis* |
| Shuttleworth, K. L. and R. F. Unz | Anoxic Or aerobic | Metal uptake (nickel, zink and copper). Calcium and magnesium competed with zink for binding sites. Lactate enhanced the uptake of nickel. | *Thiothrix* strain A1 |
| von Canstein, H., et al., | Aerobic | Mercury uptake | *P. putida* Spi3 |
| Phosphate degradation | | | |
| He, S. et al. and Ahn, J., et al., | Aerobic and anaerobic | Intercellular accumulation of phosphate in the form of poly(P) | *Candidatus Accumulibacter* |
| Kong, Y. et al. | Aerobic and anaerobic | Intercellular accumulation of phosphate in the form of poly(P) | *Actinobacteria* sp. |
| Petroleum hydrocarbon degrading | | | |
| Van Hamme, J. D. et al. | Aerobic | Naphthalene and Salicylate | *P. putida* Gpol |
| Van Hamme, J. D. et al. | Aerobic | Naphthalene | *P. putida* NCIB9816 |
| Van Hamme, J. D. et al. | Aerobic | Dibenzothiophene Naphthalene phenanthrene | *Pseudomonas* sp. strain C18 |
| Van | Aerobic | Naphthalene | *Pseudomonas* sp. Strain |

TABLE 3-continued

| Reference | Reaction type | Application | Microorganisms |
|---|---|---|---|
| Van Hamme, J. D. et al. | | | C18 |
| Van Hamme, J. D. et al. | Aerobic | Naphthalene Phenanthrene A variety of homo-hetro-and monocyclics converted to phenols | *Pseudomonas putida* OUS82 |
| Van Hamme, J. D. et al. | Aerobic | Naphthalene 2-Methynaphthalene | *Pseudomonas stutzeri* AN10 |
| Van Hamme, J. D. et al. | Aerobic | Phenanthrene | *Nocardiodes* sp. Strain KP7 |
| Van Hamme, J. D. et al. | Aerobic | Naphthalene Toluene Indene | *Rhodococcus* sp. Strain 124 |
| Van Hamme, J. D. et al. | Aerobic | Anthracene Phenanthrene Fluoranthene Pyrene, benzo [a]pyrene,1-nitropyrene | *Mycobacterium* sp. Strain PYR-1 |
| Van Hamme, J. D. et al. | Aerobic | Phenanthrene Anthracene, benzo[b]fluoranthene Naphthalene Fluoranthene, pyrene Intermediate catabolites | *Sphingomonas paucimobilis var* EPA505 |
| Van Hamme, J. D. et al. | Aerobic | n-alkylbenzene n-alakycyclohexene | *Alcanivorax* sp. Strain MBIC 4326 |
| Van Hamme, J. D. et al. | Aerobic | Naphthalene phenanthrene | *Burkholderia* sp. RP007 |
| Shen, H. and Y. T. Wang | Aerobic | Using Chromium and phenol as a sole carbon source | *P. putida* DMP-1 & *Escherichia coli* ATCC 33456 |
| Van Hamme, J. D. et al. | Anaerobic | Toluene | *Blastochloris sulfoviridis* ToP1 |
| Van Hamme, J. D. et al. | Anaerobic | Ethylbenzene | *Azoarcus* sp. Strain EB1 |
| Van Hamme, J. D. et al. | Anaerobic | Toluene, m-xylene | *Azoarcus* sp. Strain T |
| Van Hamme, J. D. et al. | Anaerobic | Toluene, m-xylene | *Azoarcus* sp. Strain Td15 |
| Van Hamme, J. D. et al. | Anaerobic | Toluene | *Azoarcus* sp. Strain To14 |
| Van Hamme, J. D. et al. | Anaerobic | Benzene, toluene | *Dechloromonas* sp. Strain JJ |
| Van Hamme, J. D. et al. | Anaerobic | Benzene, toluene | *Dechloromonas* sp. Strain RCB |
| Van Hamme, J. D. et al. | Anaerobic | Naphthalene | *Pseudomonas* sp. Strain NAP-3 |
| Van Hamme, J. D. et al. | Anaerobic | Ethylbenzene, toluene | *Pseudomonas* sp. Strain EbN1 |
| Van Hamme, J. D. et al. | Anaerobic | $C_{14}$-$C_{20}$ alkanes | *Pseudomonas* sp. Strain HdN1 |
| Van Hamme, J. D. et al. | Anaerobic | $C_6$-$C_8$ alkanes | *Pseudomonas* sp. Strain HxN1 |
| Van Hamme, J. D. et al. | Anaerobic | Toluene, m-xylene | *Pseudomonas* sp. Strain M3 |
| Van Hamme, J. D. et al. | Anaerobic | Toluene, m-xylene | *Pseudomonas* sp. Strain mXyN1 |

TABLE 3-continued

| Reference | Reaction type | Application | Microorganisms |
|---|---|---|---|
| Van Hamme, J. D. et al. | Anaerobic | $C_8$-$C_{12}$ alkanes | *Pseudomonas* sp. Strain mXyN1 |
| Van Hamme, J. D. et al. | Anaerobic | Toluene, m-xylene | *Pseudomonas* sp. Strain PbN1 |

Table 3 references:
Luque-Almagro, V. M., et al., Appl Environ Microbiol, 2005. 71(2): 940-7
Laddaga, R. A., et al., J Bacteriol, 1985. 162(3): 1106-10
Shuttleworth, K. L. and R. F. Unz, Appl Environ Microbiol, 1993. 59(5): 1274-1282
von Canstein, H., et al., Appl Environ Microbiol, 2002. 68(4): 1938-46
von Canstein, H., et al., Appl Environ Microbiol, 1999. 65(12): 5279-84
He, S. et al., Appl Environ Microbiol, 2007. 73(18): 5865-74
Ahn, J., et al., Appl Environ Microbiol, 2007. 73(7): 2257-70
Kong, Y. et al., Appl Environ Microbiol, 2005. 71(7): 4076-85
Van Hamme, J. D. et al., Microbiol Mol Biol Rev, 2003. 67(4): 503-49
Shen, H. and Y. T. Wang, Appl Environ Microbiol, 1995. 61(7): 2754-8

In order to enhance the microorganism activity in decontamination of soil or water, the inner cores of the particles may be formulated to be devoid of essential elements, such as e.g. nitrogen, specific hydrocarbons, iron, magnesium, phosphorus and sulfur, of amino acids, sugars or carbon source such as glucose, of various salts such as NaCl and of other compounds such as lactate. Elimination of such elements from the inner core will compel the microorganisms to rely on elements from the contaminated area (e.g. soil or water).

As mentioned above, the particles of the present invention may be used for the generation of various molecules of interest such as recombinant polypeptides.

Thus, according to an aspect of the present invention, there is provided a method of synthesizing a molecule of interest by contacting a single or a plurality of particles with a liquid medium (e.g in a bioreactor) under conditions (e.g. time and temperature) that allow synthesis of the molecule of interest and wherein the population of dried microorganisms within the particles is capable of synthesizing the molecule of interest on contact with the liquid medium.

As used herein the phrase "molecule of interest" refers to any molecule which is naturally or artificially synthesized by a microorganism.

According to one embodiment, the molecule of interest is a polypeptide.

As used herein the term "polypeptide" (or peptide) as used herein refers to a recombinant polypeptide or one which is naturally expressed (and preferably secreted) by the microorganisms.

Exemplary polypeptides include, but are not limited to, an antibody, an insulin, an interferon, a growth factor, a clotting factor, an enzyme, a diamine, a polyamine, an antibiotic, a glycopeptide, a lipopeptide, a hormone and a steroid.

According to another embodiment, the molecule of interest is an antibiotic.

Exemplary antibiotic agents which may be synthesized according to the present teachings include but are not limited to, penicillins (e.g. penicillin G, ampicillin and amoxicillin) cephalosporins (e.g. cephalexin, cefaclor and cefixime), carbapenems (e.g. meropenem and ertapenem), aminoglycosides (e.g. streptomycin, kanamycin, neomycin, tobramycin and gentamycin), macrolides (e.g. erythromycin, azithromycin and clarithromycin), lincosamides (e.g. clindamycin), streptogramins (e.g. quinupristin and dalfopristin), fluoroquinolones (e.g. ciprofloxacin, levofloxacin and norfloxacin), lincomycins, tetracyclines (e.g. chlortetracycline, oxytetracycline and doxycycline), chloramphenicol, griseofulvin, rifampin, mupirocin, cycloserine, polymyxine and aminocyclitols.

The microorganisms of the present invention may be genetically modified such that they may synthesize the desired molecules (e.g. hormone or antibiotic). Thus, for example, the microorganism may be genetically modified to express an enzyme or several enzymes which allows for the production of the hormone or antibiotic.

According to another embodiment, the microorganism may be modified to secrete an enzyme which migrates out of the particle into the medium where it catalyzes the production of a target agent (e.g. an antibiotic).

Any method known to one of ordinary skill in the art for genetic modification of an organism may be used according to the present teachings. Such methods include recombinant DNA technology as described for example in Studier et al. (1990) Methods in Enzymol. 185:60-89 and in U.S. Pat. No. 5,932,447.

The recombinant polypeptides and other contemplated molecules may be generated in vitro in mass production (e.g. in bioreactors) or in small quantities or home use (e.g. in small containers). For mass production, the particles are placed in a liquid medium (e.g. culture medium) preferably under sterile conditions; the polypeptides are secreted into the liquid medium and are purified prior to administration to the subject.

The present invention contemplates generating more than one molecule (e.g. recombinant polypeptide) in a single bioreactor. In this case, the microorganisms in each particle synthesize only one type of molecule. According to one embodiment, the particle is fabricated such that the molecule is not capable of exiting through the outer membrane into the medium—so as to avoid the different molecules (e.g. recombinant polypeptides) mixing in the bioreactor. According to another embodiment, the molecule (e.g. recombinant polypeptide) is not secreted by the microorganisms, such that it is maintained in the particle (i.e. does not exit the particle). In order to distinguish between the different polypeptides, the particles may be labeled (as depicted in FIG. 19A) as for example with a detectable moiety such as a radioisotope, a fluorescent or chemiluminescent compound or a tag. Alternatively, the particles may be cultured in a separate area in the bioreactor system (e.g. in divided internal chambers of a bioreactor, see FIG. 19B).

Separation and purification of the molecules from the liquid medium may be carried out using any method known to one of ordinary skill in the art as for example by high-performance liquid chromatography (HPLC), normal phase HPLC (NP-HPLC), reversed phase HPLC (RPC) or size exclusion chromatography (SEC), based on their idiosyncratic polarities and interactions with the column's stationary phase (e.g. hydrophobic saturated carbon chains). Preferably the molecules are purified under sterile conditions. As mentioned above, the particles of the present invention may also be beneficial for generating molecules (e.g. polypeptides) with short half-lives. Such particles may be valuable when only small amounts are required e.g. for home or clinic uses. The particles may be placed in a small bioreactor (e.g. glass, bottle) with liquid medium. Following a finite amount of time (e.g. overnight), the liquid medium comprises the molecules of interest (since they have been secreted into the liquid medium by the microorganisms). The liquid medium may be administered to the subject without any intermediate steps (e.g. topically). The particles may be used for several weeks (e.g. 3-4 weeks) while the liquid medium may be used and replaced (e.g. with a fresh medium).

Alternatively, the molecules may be generated in vivo. In such cases, the particles are administered to the subject and synthesis of the molecules occurs inside the body. The molecules may be directly secreted from the particle to the diseased area, as explained herein below.

Accordingly, the present invention contemplates the use of the particles for treating medical disorders, such as gastrointestinal disorders, in a subject in need thereof.

As used herein the term "treating" refers to preventing, curing, reversing, attenuating, alleviating, minimizing, suppressing or halting the deleterious effects of the disease e.g. gastrointestinal disease. Those of skill in the art will understand that various methodologies and assays can be used to assess the development of a pathology, and similarly, various methodologies and assays may be used to assess the reduction, remission or regression of a pathology.

As used herein the phrase "a subject in need thereof" refers to a mammal, preferably a human subject, male or female of any age, who has been diagnosed with probable or definite gastrointestinal disease, e.g., a subject who experienced inflammatory colon disease. The diagnosis of a gastrointestinal disease may include any diagnosis test as, for example, laboratory tests, endoscopic evaluation, biopsies of the mucosa (e.g. for ulcerative colitis), barium follow-through x-ray (e.g. for Crohn's disease), and CT or MRI scans (e.g. for Crohn's disease).

As used herein the term "gastrointestinal disorder" refers to any disease that pertains to the gastrointestinal tract, also referred to as digestive diseases. These include diseases of the esophagus, stomach, first, second and third part of the duodenum, jejunum, ileum, the ileo-cecal complex, large intestine (ascending, transverse and descending colon) sigmoid colon and rectum.

Examples of such diseases include, but are not limited to, gastrointestinal tumors, inflammatory diseases, chronic inflammatory intestinal diseases, gastrointestinal diseases, autoimmune diseases of the gastrointestinal tract, intestinal diseases, chronic inflammatory intestinal diseases (Garcia Herola A. et al., Gastroenterol Hepatol. 2000 January; 23 (1):16), chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

It will be appreciated that for treatment of a disorder the microorganisms within the particles of the present invention are selected as those capable of producing and secreting an agent (e.g. a polypeptide, an antibiotic) such as an agent useful for the treatment of a gastrointestinal disorder.

Thus, the particles of the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the particles accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

According to a specific embodiment of the present invention, the particles are administered orally.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

It will be appreciated that the particles of the present invention may be coated with a soluble material (e.g. for pH control such as eudragit polymer) to allow molecule release in a specific area in the gastrointestinal tract.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (i.e. particles) effective to prevent, alleviate or ameliorate symptoms of a disorder (e.g., gastrointestinal disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to levels of the active ingredient which are sufficient to effectively regulate gastrointestinal disease treatment. Dosages necessary to achieve the desired effect will depend on individual characteristics and route of administration. Detection assays can be used to determine disease manifestation.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. The dosage and timing of administration will be responsive to a careful and continuous monitoring of the individual changing condition.

Models for gastrointestinal diseases include e.g. animal models for inflammatory colon diseases such as of ulcerative colitis including trinitrobenzene sulfonic acid (TNBS)-induced colitis in rats and mice [Komori et al., J Gastroenterol (2005) 40: 591-599].

According to the present invention at least one particle is administered to the subject to treat the gastrointestinal disorder. However, several particles may be administered as necessary. The particles may be administered concomitantly, or separately such a on the same day, or on different days, weeks or months as necessary.

Regardless of the above, the particle is administered at an amount selected to avoid unwanted side-effects.

It will be appreciated that the particles of the present invention are preferably secreted via the subject's stool following a few hours to several days of administration thereof.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Another possible application of the particles of the present invention is for cosmetic applications. Thus, the particles of the present invention can be used as a supplement in a variety of cosmetics, as for example, to secrete substance (e.g. polypeptides) which may be used as is or added to cosmetics.

Cosmetics are substances used to enhance or protect the appearance or odor of the human body. Examples of cosmetics include skin-care creams, lotions, powders, perfumes, lipsticks, fingernail and toe nail polish, eye and facial makeup, perfumes, aftershaves, manicures, permanent waves, shaving foams and creams, hair colors, hair sprays and gels, deodorants, baby products, bath oils, bubble baths, bath salts, butters and many other types of products.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed.

(1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Particle Manufacture

Materials and Experimental Procedures
Freeze-Dried Microorganism (Bacteria) Manufacture
Inventors used a freeze-dry method to produce a dry bacteria/microorganism powder according to previously described protocols [Leslie, S. B., et al., Appl Environ Microbiol (1995) 61(10): 3592-7; Sinskey, T. J. and G. J. Silverman, J Bacteriol (1970) 101(2): 429-37; Morgan, C. A., et al., J Microbiol Methods (2006) 66(2): 183-93; Costa, E., et al., J Appl Microbiol (2002) 92(5): 873-8]. The following steps were carried out:

1) Bacteria (*E. coli* TG1, *E. coli* TG1 pChv1, or *E. coli* DH5α) were grown overnight at 37° C., 200 rpm, 18 h, in 1 L growth medium comprising 0.5% yeast extract, 1% tryptone, 0.5% NaCl, and 5% sucrose (as a protecting freeze agent).

2) The culture was centrifuged (10 min, 7000 g, 4° C.).

3) The culture was suspended in 8 ml ice cold phosphate buffer solution (PBS, Sigma).

4) The suspended culture was centrifuged (10 min, 7000 g, 4° C.).

5) The culture was suspended in 8 ml ice cold PBS comprising 5% sucrose.

6) Steps 4-5 were repeated.

7) The culture was incubated at room temperature (22° C.) for 20 minutes, and was then divided into 1 ml doses for future viability counts (saving the precise volume).

8) The culture was incubated for 48-72 h at −80° C.

9) The culture was freeze-dried for 52 h (1 Pa, −45° C., 10 µHg).

9) The dried culture was then stored at room temperature inside a dissector.

Inner Core Design and Manufacture
The inner cores were made of LA (Luria Agar-0.5% yeast extract, 1% tryptone, 0.5% NaCl and 0.185% agar) which were cast into 96 wells plates. After the polymerization of the LA, the inner cores were released from the plates onto petri dishes for drying in a biological hood for 72 hours. Next, the inner cores were sterilized using U.V radiation within the biological hood for several hours.

Other Inner Particle Components
Glass beads (1 mm diameter) were added to the particles to increase the weight of the particle and to provide additional surface area for biofilm formation.

The Particle Construct
Gelatin capsules, size 000, were used to integrate all the inner components (microorganisms, inner core and glass beads) and to provide the foundation to built the outer membrane of the particle.

Constructing the Outer Membrane
Two types of polymers were used to construct the outer membrane, ethyl cellulose and cellulose acetate as follows:

Ethyl Cellulose (EC) Outer Membrane Coating
Ethyl cellulose polymer solution was prepared using a mix of two solvents, methanol and acetone, along with a plasticizer such as caster oil.

The protocol of the polymer solution:
Solution solvents (92%): 80% acetone and 20% methanol.
Suspended solids (8%): caster oil (12%) and ethyl cellulose (88%) (TAIAN RUITI CELLULOSE LTD., China).

The prepared solution was mixed with a stirrer for at least half an hour. Next, the inventor used a spray to coat the gelatin capsules with the polymer. The particles were put on an upside down 96-well plate and sprayed 4-5 times on each side. The polymer solution volume was calculated according the required thickness of the particle (determined according to the required resistance for a cutting force for a given time). The inventor used 13 ml or 15 ml of the polymer solution for coating of one particle. For ethyl cellulose, 6% and 8% suspended solids were used within the polymer solution and the stability of both formulations was tested.

Cellulose Acetate Outer Membrane Coating
The cellulose acetate polymer solution was prepared using a mix of two solvents, methanol and acetone, along with a plasticizer such as caster oil.

The protocol of the polymer solution:
Solution solvents (92%): 80% acetone and 20% methanol.
Suspended solids (8%): caster oil (12%) and cellulose acetate (88%) (EASTMAN, Switzerland).

The prepared solution was mixed with a stirrer for at least half an hour. Next, the inventor used a spray to coat the gelatin capsule with the polymer. The particles were put on an upside down 96-well plate and sprayed 4-5 times on each side. Each particle was coated with 8 ml of the polymer solution.

Figure 1A:
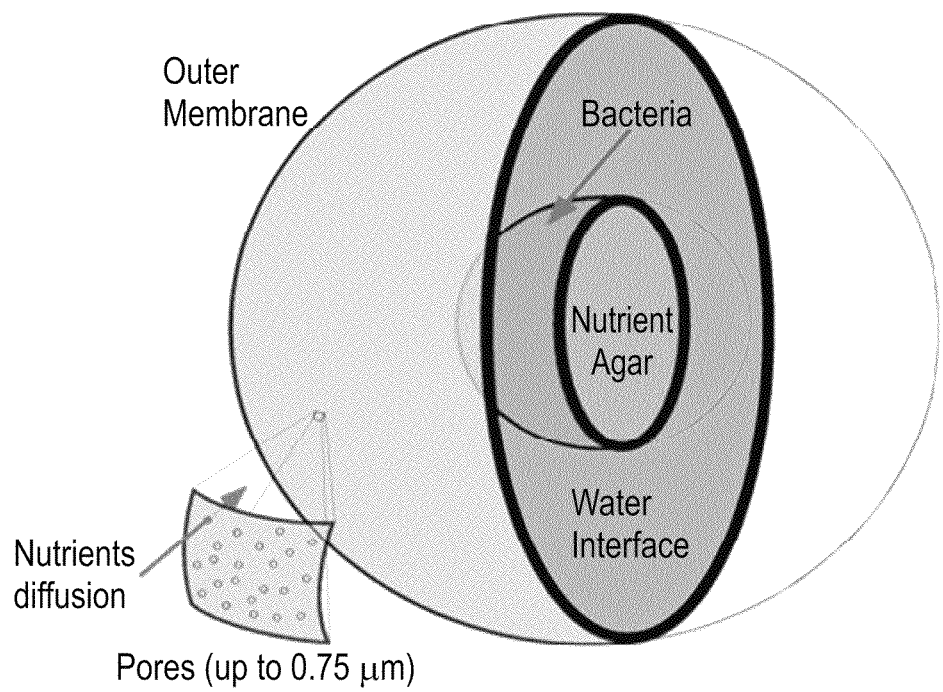
Figure 1B:
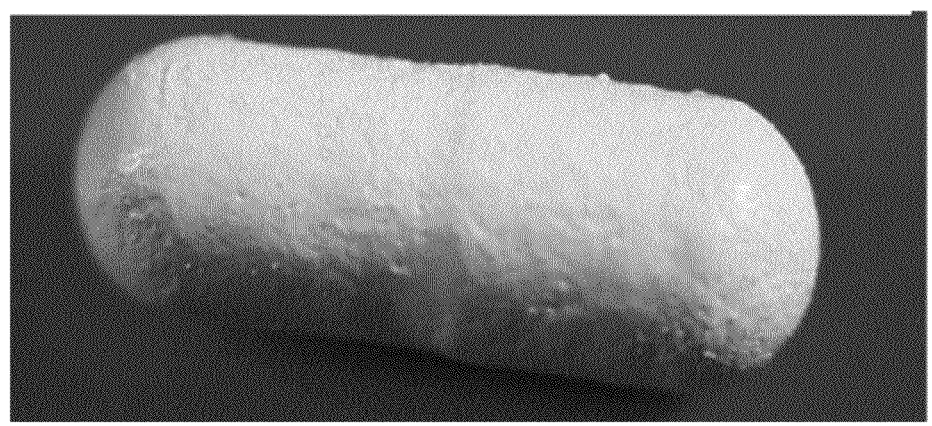

Results
The particle generated according to the present teachings comprised the following physical components: the outer membrane, the inner core and the microorganisms. Each component was prepared separately (except for the outer membrane). All of the inner components: the inner core, the glass beads and the microorganisms (e.g. bacteria) were integrated inside a gelatin capsule (size 000) and the outer membrane was constructed on the surface of the gelatin capsule (as described in detail in the Materials and Experimental procedures section above). FIG. 1B presents an example of a particle prototype generated according to the present invention.

Manufacture of Freeze-Dried Bacteria
Since the product of the present teachings was designed to have a long life span, the inventor used freeze-dried bacteria/microorganism which is known to be a preferred method for transporting and storing cultures of microorganisms. FIG. 2 presents the viability at different time intervals (weeks) after rehydration. As shown in FIG. 2, the dried culture showed stability for at least 5 weeks after rehydration. Moreover, the bacterial viability levels were kept above 7,500,000,000 bacteria per milliliter which is a preferred concentration for processing and for reducing culture contamination. The weight of 1 ml freeze-dried bacteria culture was 0.07 gr. The freeze-dried culture texture was observed as illustrated in FIG. 3.

Inner Core Design and Manufacture

The aim of the inner core inside the particle was to provide feeding nutrients to the culture and to provide additional biofilm formation surface area. LA (Luria Agar), a rich nutrient supplier solid agent for bacterial growth and prosperity and a surface area for biofilm formation, was used to generate the inner cores. FIG. 4A shows the inner cores after polymerization (on left) and in comparison to a dry core (on right). FIG. 4B depicts a lateral view of the inner core after polymerization and after sterilization.

Other Inner Particle Components

The rate of activation of the particle of the present invention depended on the penetration rate of water molecules into the particle. In order to prevent the particles from floating on the surface of the medium (which may cause delayed activation and loss of particle surface area—reduce the contact area with the medium), and to provide additional surface area for biofilm formation, inventors added glass beads to the particles.

The Particle Construct

The inventor of the present invention used a gelatin capsule (size 000) to integrate all of the inner components (microorganisms, inner core and glass beads) and to provide the foundations on which to build the outer membrane (see FIG. 5).

Constructing the Outer Membrane

The inventor of the present invention used two types of polymers to construct the outer membrane, ethyl cellulose and cellulose acetate, and hence, constructed two types of particle prototypes. Ethyl cellulose or cellulose acetate, water insoluble porous polymers, were prepared as described in detail in the Materials and Experimental procedures section above. The particles were sprayed with ethyl cellulose or cellulose acetate by placing the particles on an upside down 96 wells plate and spraying each side 4-5 times with the desirable polymer (as shown in FIG. 6). As depicted in FIG. 7, particles coated with 8% cellulose acetate displayed 1-3 weeks of stable coating.

Example 2

Particle Activation and Biocompatibility

Materials and Experimental Procedures
Particle Manufacture

Particles were prepared as described in Example 1, hereinabove.

Particle Activation and Biocompatibility

In order to activate the particles, the ethyl cellulose or cellulose acetate coated particles were placed in bottles containing PBS or Saline for different time periods.

Water content inside the particles was measured as a means to evaluate water flow rate. Particles weights were measured using a scale at different time intervals and estimation of the particle water content was calculated as percentage of the maximum weight of a filled water particle (the weight of a particle after the particle was filled with water).

Bacteria viability was measured by first collecting a sample of the liquid inside the particle using a syringe and needle. The sample supernatant was measured and diluted in saline (0.9 ml of saline was added to 0.1 ml sample) to produce culture viability counts in a LA nutrient plate. The inner core was analyzed for morphology and for viability. The solid phase of the particle which included the glass beads and the inner cores, were kept in an eppendorf tube and suspended in 1 ml of saline and vortexed for 30 seconds to remove all of the bacteria therefrom. Viable count was then performed on the supernatant as described above.

Results

Since the biological process of the present invention can only be activated when the bacteria is transferred from a dry state to a liquid suspended state (planktonic state), liquid flow into the particle is an essential step. The goal of the present invention was to ensure that particle activation time was no more than several hours. In order to evaluate the particle activation time, the present inventor measured the weight of the particle at particular time intervals and estimated the particle water content as percentage of the maximum weight of a filled water particle (the weight of a particle after the particle was filled with water, the percentage of particle water content of the maximum water content −1.4 gr). Analysis of the results illustrated that 30% of the particle water content was the point of particle activation, as was demonstrated on a particle that was coated with 8% ethyl cellulose.

FIG. 8 summarizes the comparison results of the water flow rate between 15 ml and 13 ml coated 8% ethyl cellulose particles. As shown in FIG. 8, the present results indicated that ethyl cellulose 8% (15 ml) coated particles had a faster particle activation rate. Particle activation of 15 ml coated Ethyl cellulose membrane (8%) was achieved after 72 h as compared to 96 h for 13 ml coated particles. Moreover, particles that were coated in 15 ml of the polymeric solution reached their maximum weight (106%) while particles coated with 13 ml reached only to 87% of the maximum particle weight. Thus, the maximum particle weight was 2.04 gr and the maximum water content within the particle was 1.4 gr water. Non-activated particle weight was 0.64 gr (for 15 ml coated capsules) or 0.41 gr (for 13 ml coated capsules). After 4 weeks, the ethyl cellulose coated particles were slightly expended (FIG. 7A). Particles devoid of bacteria showed a significant inhibition in water penetration. These results suggest that the bacteria protective agent (a sugar) used for freeze-drying generated an osmotic pressure which accelerated the water flow rate into the particle.

Cellulose Acetate membranes (8%) were examined to estimate the activation time point. The present inventor examined particles coated with 8 ml cellulose acetate (8%), filled with different types of bacteria: *E. coli* TG1 and *E. coli* TG1 pChv1. As shown in FIG. 9, the bacteria type had no influence on water flow into the particles. The activation time point of both of the cellulose acetate membrane particles was between 48-72 h.

Comparison of water flow rate between ethyl cellulose and cellulose acetate particles (FIG. 10) illustrates a slightly faster rate of particle activation in cellulose acetate coated particles.

The main goal of this experiment was to evaluate the biocompatibility of the bacterial culture inside the particle, which effects both the product life span prior to and following activation. In order to assess biocompatibility, the inventor placed the different particles in saline (see FIGS. 11A-C). The particles were maintained in the saline for 5 weeks and the liquid inside the particles was checked on a weekly basis by collection using a syringe and needle. The collected sample volume was then measured and diluted in saline to produce culture viability counts in LA nutrient plate. The inner core was assessed for both morphology and for viability. The glass beads and the inner cores were kept in an eppendorf tube and suspended in 1 ml of saline and vortexed for 30 seconds to remove all of the bacteria therefrom prior to viability counts. Viability was measured in the supernatant as described above.

Viability of the inner core typically showed reduction of one log compared to the liquid viability (data are not shown). This indicated that inner cores (two in one particle) were crucial for the stability of the culture inside the particle and had a great contribution to the overall bacteria counts inside the particle. The liquid (planktonic) bacteria population (after particle activation) could originate from several sources: A. Starter—the inserted freeze-dried culture, B. Planktonic bacteria reproduction, or C. Inner core bacteria migration to the liquid phase.

The bacteria viability within particles (i.e. not in the solid phase of the particle) of two culture productions which were coated with cellulose acetate (8%) are depicted in FIG. 12. As shown in FIG. 12, after 5 weeks of particle incubation in saline, the bacteria culture remained stable at an average concentration of 8 log 10 CFU/ml. This concentration was considered high and provided sufficient biological process. Furthermore, these high bacterial levels could eliminate possible contamination of the particle (by other microorganisms) as the bacteria occupy the majority of the surface area of the inner core (i.e. the only food source within the particle which was incubated in saline). Thus, the cellulose acetate particle presented good biocompatibility for at least 5 weeks after activation.

Ethyl cellulose-coated particles were also tested for viability. FIG. 13 shows the viability of an *E. coli* TG1 culture within these particles at different time intervals. A typical bacterial growth curve was observed by the bacterial culture within the particle. Thus, in the first week an environment culture adaptation of the bacterial culture was observed which was followed by logarithmic phase for more than 1 week. The decrease in the curve (from 2 weeks to 4 weeks) presented a withdrawal in the bacteria concentration number. After 4 weeks, the culture concentration was 10,000,000 bacteria per 1 ml liquid. This bacterial concentration is sufficient to provide a desirable biological process.

Thus, both the cellulose acetate and ethyl cellulose coated particles presented good bacterial biocompatibility for at least 4 weeks of incubation in saline.

Example 3

Macromolecules Trafficking Validation

Materials and Experimental Procedures
Preparation Bacteria

A bacterial culture (*E. coli* TG1) harboring a molecular marker was used to evaluate molecule trafficking across the particle membrane. The molecular marker used was a plasmid (pChv1-13 kbp) that contained the entire luciferase system derived from Vibrio fischeri. In the presence of the system inducer (Homo serine lactone—C10 hydrocarbon, see FIG. 14), the plasmid is activated and transcription and translation of the luciferase enzyme is accomplished. Luciferase catalyzes the metabolic reaction of transferring fatty acids into aldehydes. The byproduct of this reaction is light emission (480 nm) which may be measured by a spectrophotometer.

The Membrane Permeability Validation System

Two systems were used: 1) the experimental system in which the inducer (1 μg/ml) was added to the particle medium (saline), and 2) the control system which did not contain the inducer in the particle medium (as shown in FIG. 15). The particles were incubated inside each of the mediums for one hour prior to extraction of the particle inner medium (containing the planktonic bacterial culture) using a syringe with a needle. The sample was read in a Bio-Tek spectrophotometer (light detector sensitivity 125). Light emission was measured in the test culture, the control system and a blank medium (saline).

Results

Light emission was measured for the experimental system which contained the inducer, the control system and a blank medium (saline). Significant light emission of the test system represented penetration of the inducer and gene activation of the molecular luciferase system within the bacterial culture. Table 4, below, shows the light emission results obtained. The results indicate that the inducer penetrated the particles in less than 40 minutes (measured from the addition of the inducer). It may be estimated that it takes at least 20 minutes to activate the molecular marker. After one hour of incubation, light emission in the experimental system (comprising the inducer) was higher by more than 7 times in comparison to the control system which did not contain the inducer in the particle medium.

It may be concluded that cellulose acetate membranes comprise a porosity which allow molecules of the size of the inducer to be transported from the medium to the particle and back. Furthermore, the bacterial culture within the particle remained stable for at least two weeks.

TABLE 4

Results of light emission

| Luminescence ratio (%) | Sample #2 | Sample #1 | Control #2 | Control #1 | Blank #2 (saline) | Blank #1 (saline) |
| --- | --- | --- | --- | --- | --- | --- |
| 308% | 1935 | 2037 | 615 | 673 | 597 | 559 |
| 307% | 1967 | 2088 | 664 | 659 | 592 | 533 |
| 340% | 2135 | 2044 | 652 | 584 | 511 | 521 |
| 361% | 2192 | 2193 | 558 | 658 | 524 | 568 |
| 509% | 2659 | 2712 | 562 | 493 | 537 | 496 |
| 463% | 2758 | 2634 | 572 | 592 | 563 | 493 |
| 479% | 3150 | 3100 | 666 | 638 | 519 | 573 |
| 731% | 5190 | 5191 | 723 | 696 | 602 | 582* |

Light emission results of the test system, the control system and blank (saline). After half an hour the ratio between light emission of the test group and the control group was 7 times higher.
*The last reading was made after half an hour since the first read Example 4

Petroleum Wastewater Treatment Indication

Materials and Experimental Procedures

Product Manufacture

A particle, suitable for petroleum wastewater treatment, was manufactured under semi-sterile conditions (designated herein as NatiCap petroleum) as follows:

1) The inner core components included: 3 glass beads, 2 dry inner cores (nutrient agar, LA), a bacterial blend, a commercial microbial blend (USAbioproducts—biotreat type 4) which included selected adapted high potency microbes for biological biodegradation of petroleum hydrocarbons, and additional components including activated Carbon (dusk form) and degradation enzymes. All of the inner core components were inserted into a water-soluble gelatin capsule.

2) The gelatin capsule comprising all of the inner core components was coated with cellulose acetate 8% polymer (15 ml per particle) as described in detail in Example 1, hereinabove.

NatiCap Petroleum Activation

In order to activate the product, 75 particles of the NatiCap petroleum were placed in a 1 L container containing 500 ml of saline. The particles were incubated for 24 h prior to the experiment (after 24 h of activation the average weight of the particle was 1.88 gr, while the average dry particle weight was 1.067 gr-58% of water content).

The Model Test

The wastewater efficacy test was carried out in a bioreactor which was designed as follow:

The bioreactor was made of PVC: 40 cm×20 cm×25 cm. Two air pipes located 5 cm above the bottom of the bioreactor were spread lengthwise and contained air diffusers (one air diffuser every 5 cm). Both air pipes shared a common entry into the bioreactor. The air flow rate thru the air pipes was 550 liters per hour (using an air pump, Sere 550). The purpose of using air diffusers inside the bioreactor was to achieve good oxygen solubility in the wastewater and to generate fluid circulation. The test Process Flow Diagram (PFD) as used is depicted in FIGS. 16A-C. Sampling was completed through a valve at 12.5 cm (measured from the bottom of the reactor).

The wastewater tested was obtained from a refinery (Haifa, Israel). Prior to testing, the wastewater was treated with an API (water/oil separator) and DGF (Dissolved Gas Flotation) which decreases the emulation and suspends solids inside the wastewater.

Methods

75 NatiCap petroleum particles were activated in 500 ml of saline and added to the bioreactor which contained 15 liters of the petroleum wastewater. Thus, the total fluid volume in the first cycle of the bioreactor was 15.5 litters. The particle/volume ratio was 1:200 ml. Prior to the addition of the particles, the wastewater was sampled.

Conditions in the bioreactor were cycled as follows: 72 hours of aerobic reaction conditions (air diffusers—550 liters per minute) followed by 72 hours of anoxic conditions (without activating the air diffusers). For each new cycle (after 144 hours) the treated wastewater was replaced with fresh petroleum wastewater (from the same source). The test experiment included 3 cycles (for a total of 18 days).

Sampling points:
1. Prior to the experiment (referenced for each cycle).
2. After 72 hours (aerobic stage).
3. After 144 hours (at the end of the anoxic stage).

Prior to wastewater sampling and the cycling waste exchange, the wastewater was air vortexed for 0.5 hour.

Bacterial viability was tested by adding the particle sludge into a vial (estimated volume of 1 ml) and 0.5 ml of saline. Serial dilutions with saline were performed and seeded on a nutrient agar (LA) using the Derigalski method [M. E. Madigan, J. M. Martinko, J. Parker, Microorganisms, 12th ed. (2000) Prentice Hall, Upper Saddle River, N.J.].

Results

Laboratory Chemical Analysis of the Wastewater

COD (chemical oxygen demand) was measured as an indirect indicator for PTH (petroleum hydrocarbon) concentration reduction.

Cycle 1: At the end of the first cycle (144 h after incubation of the active particles in the wastewater), the present inventor observed only one broken particle and 16 of the particles were floating. One of the floating particles was removed for fluid content analysis of the bacterial composition (Pseudomonas Vs. Bacillus) and for inner core analysis. A black sludge (the active carbon and microorganisms mix) was observed inside the particle. The inner cores tested were wet, indicating massive fluid penetration.

Bacterial viability performed after 144 hours of treatment showed a bacterial concentration of about $10^9$-$10^{12}$ CFU/ml. The bacterial mix culture contained at least 5 population types (microorganism population diversity). Table 5 (below) presents the results of the bacterial viability of a NatiCap petroleum particle. Moreover, the wastewater (medium) became cloudier indicating the presence of planktonic bacteria. After centrifugation (1.5 minutes, 13,000 rpm) of 1 ml of the treated wastewater, a 0.5 mm white pellet was obtained and the medium was clear, indicating significant presence of planktonic microorganisms (natural wastewater flora). Thus, it may be postulated that during the incubation time, particularly at the anoxic stage, a rich bacterium population developed (within the medium), probably due to a viable organic Carbon source derived from the breakdown of the petroleum hydrocarbons by the particles. This result indicates that the particle effects the PTH by chapping the molecules into smaller hydrocarbon chains so as to generate a viable Carbon source for the natural wastewater flora. Accordingly, the chemical analysis results (after 3 days, at the end of the aerobic stage) indicate a significant reduction in the concentration of COD (chemical oxygen demand—from 335 mg/l to 270 mg/l, data not shown), indicating possibly reduction in PTH concentrations. Moreover, the following analysis tests performed exhibited an increase in biomass within the wastewater (planktonic microorganisms outside the particles): BOD (biological oxygen demand) test showed a shift from 60 mg/l to 105 mg/l (data not shown) and TSS (total suspended solids) showed a shift from 10 mg/l to 20 mg/l (data not shown). After the anoxic stage (at the end of the 6 day treatment), the chemical analysis of the wastewater indicate a significant increase in COD values. These results indicate that the anoxic stage at this point was not due to the treatment.

Cycle 2: The chemical analysis results (after 3 days—at the end of the aerobic stage) indicate a reduction in COD concentrations (from 335 mg/l to 300 mg/l, data not shown), indicating a possible reduction in PTH concentrations. As shown for the first cycle, the anoxic treatment stage did not contribute to the treatment and the COD results became much higher (up to 685 mg/l, data not shown).

Cycle 3: The chemical analysis results (after 3 days—at the end of the aerobic stage) indicate a significant reduction in the concentration of COD (from 335 mg/l to 225 mg/l, data not shown), indicating a possible reduction in PTH concentrations. As shown for the first cycle, the anoxic treatment stage did not contribute to the treatment and the COD results became much higher (up to 385 mg/l, data not shown).

Bacterial Viability within the Particle

After one cycle of the experiment (144 h after incubation of the active particles in the wastewater), one particle was taken and examined in order to estimate the bacterial colony forming units and the bacterial population diversity.

TABLE 5

Bacterial viability

| Discretion of the colonies (microorganisms population diversity) | Number of bacteria colony | Dilution |
|---|---|---|
| 5 (big white colonies, Yellow, white small colonies, white with clear end colonies, fungi). | $5 * 10^9$ (cfu/ml) | $10^{-6}$ |
| 4 (white, Yellow, white small colonies, white with clear end colonies). | $4 * 10^{10}$ (cfu/ml) $3.2 * 10^{10}$ (cfu/ml) | $10^{-7}$ |
| 3 (white, Yellow, white small colonies) | $1.8 * 10^{11}$ (cfu/ml) | $10^{-8}$ |
| 3 (white, Yellow, white small colonies) | $5 * 10^{11}$ (cfu/ml) | $10^{-9}$ |
| 3 (white, Yellow, white small colonies) | $6 * 10^{12}$ (cfu/ml) $3 * 10^{12}$ (cfu/ml) | $10^{-10}$ |

As depicted in Table 5, above, the bacterial viability within the particle indicate very good microorganism prosperity after a short period of activation (a bacterial concentration of about $10^9$-$10^{12}$ CFU/ml). These results indicate a good sludge within the particles.

Taken together, the results of the NatiCap petroleum experiment showed an indirect reduction in PTH concentration (significant COD concentration reduction, up to 33% reduction) in the aerobic stage of all of the treatment cycles. Significant increases in BOD and TSS (in both aerobic and anoxic stages) indicate a massive microorganism growth within the medium. Moreover, the NatiCap petroleum exhibited good biocompatibility after 1 week. The sludge exhibited within the particle was of good quality and the bacterial concentration within the particle was up to $10^{12}$ cfu/ml. Furthermore, the biomass within the particles developed within a short period (3 days), which was efficient in treatment of petroleum wastewater, and the particle structure was stable and active for 3 weeks within the petroleum wastewater.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A particle comprising:
    (i) at least one inner core which comprises a solid matrix of nutrients for microorganism growth;
    (ii) an inner membrane being fabricated from a water-soluble polymer, said inner membrane surrounding said inner core, said inner core comprising a population of dried microorganisms; and
    (iii) an outer porous membrane surrounding said inner membrane, said outer porous membrane being insoluble in water.
2. The particle of claim 1, wherein said microorganisms comprise bacteria.
3. The particle of claim 2, wherein said bacteria comprise freeze-dried bacteria.
4. The particle of claim 1, wherein said solid matrix of nutrients comprises an agar.
5. The particle of claim 1, wherein said inner core further comprises an agent selected from the group consisting of an amino acid, an enzyme, a sugar, an iron, a salt and an essential element.
6. The particle of claim 1, wherein said inner core is devoid of at least one agent selected from the group consisting of an amino acid, a sugar, an iron, a salt and an essential element.
7. The particle of claim 1, wherein said inner membrane further comprises activated carbon granules or activated carbon chips within.
8. The particle of claim 1, wherein said water-soluble polymer comprises gelatin.
9. The particle or method of claim 1, wherein said outer porous membrane is fabricated from a polymer selected from the group consisting of PVAL (polyvinyl-alcohol), Polyethersulfone (PES), Cellulose Acetate, Cellulose Nitrate, Ethyl Cellulose, Nitrocellulose Mixed Esters, Polycarbonate film, Nylon, PVDF (poly(vinylidene fluoride)) and Polysulfone.
10. The particle of claim 1, wherein said outer porous membrane is fabricated from a polymer comprising Cellulose Acetate.
11. The particle of claim 1, wherein said outer porous membrane is fabricated from a polymer comprising Ethyl Cellulose.
12. The particle of claim 1, wherein said porous membrane is resistant to biofilm formation.
13. The particle of claim 1, wherein a pore of said porous membrane is less than 0.85 µM.
14. The particle of claim 1, wherein said particle is between 0.5-30 cm in length.
15. The particle of claim 1, wherein said solid matrix of nutrients comprises an agar, said water-soluble polymer comprises gelatin and said outer porous membrane is fabricated from a polymer comprising Cellulose Acetate.
16. A method of generating the particle of claim 1, the method comprising:
    (a) inserting a solid matrix of nutrients for microorganism growth inside a membrane fabricated from a water-soluble polymer;
    (b) inserting a population of dried microorganisms into said membrane; and
    (c) covering said membrane with a water-insoluble porous membrane, thereby producing the particle.
17. A method of propagating a population of microorganisms, the method comprising:
    (a) contacting the particle of claim 1 with a liquid under conditions that allow said liquid to penetrate said outer porous membrane and wet said dried microorganisms so as to generate an activated particle; and
    (b) culturing said activated particle, thereby propagating said population of microorganisms.
18. A method of purifying water, the method comprising contacting the water with at least one particle of claim 1 under conditions that allow said microorganisms to decontaminate the water, thereby purifying the water.
19. The method of claim 18, wherein said water is wastewater.
20. The method of claim 18, wherein said water is drinking water.
21. The method of claim 18, wherein said at least one particle comprises at least two non-identical particles.
22. The method of claim 21, wherein said non-identical particles comprise different populations of microorganisms.
23. A method of treating soil contamination, the method comprising:
    (a) contacting at least one particle of claim 1 with a liquid under conditions that allow said liquid to penetrate said outer porous membrane and wet said dried microorganisms to generate an activated particle; and
    (b) contacting the soil with said activated particle, thereby treating the soil contamination.
24. A method of synthesizing a molecule of interest, the method comprising: contacting a plurality of particles with a liquid medium under conditions which allow synthesis of the molecule of interest, wherein each of said plurality of particles comprise:
    (i) a population of dried microorganisms;
    (ii) an inner membrane being fabricated from a water-soluble polymer, said inner membrane comprising said population of dried microorganisms, wherein said population of dried microorganisms are capable of synthesizing the molecule of interest on contact with said liquid medium; and
    (iii) an outer porous membrane surrounding said inner membrane, said outer porous membrane being insoluble in water thereby synthesizing the molecule of interest.

* * * * *